United States Patent
Rosenberg et al.

(10) Patent No.: US 8,221,781 B2
(45) Date of Patent: *Jul. 17, 2012

(54) OSTEOINDUCTIVE BONE MATERIAL

(75) Inventors: Aron D. Rosenberg, Brookline, MA (US); Laurent D. Gilles de Pelichy, Allston, MA (US); Daniel Egan, Ayer, MA (US); Aliassghar N. Tofighi, Waltham, MA (US); Dosuk D. Lee, Brookline, MA (US)

(73) Assignee: Etex Corporation, Cambridge, MA (US)

( * ) Notice: Subject to any disclaimer, the term of this patent is extended or adjusted under 35 U.S.C. 154(b) by 1051 days.

This patent is subject to a terminal disclaimer.

(21) Appl. No.: 10/822,540

(22) Filed: Apr. 12, 2004

(65) Prior Publication Data
US 2005/0084542 A1 Apr. 21, 2005

Related U.S. Application Data

(60) Provisional application No. 60/462,416, filed on Apr. 11, 2003.

(51) Int. Cl.
*A61F 2/28* (2006.01)
*A61F 2/26* (2006.01)
(52) U.S. Cl. ...................................... 424/426
(58) Field of Classification Search .................. None
See application file for complete search history.

(56) References Cited

U.S. PATENT DOCUMENTS

| | | | |
|---|---|---|---|
| 2,967,802 A | 1/1961 | Towey et al. | |
| 3,608,071 A | 9/1971 | Relyveld et al. | |
| 3,925,545 A | 12/1975 | Relyveld | |
| 4,016,252 A | 4/1977 | Relyveld | |
| 4,108,690 A | 8/1978 | Heller | |
| 4,110,432 A | 8/1978 | Wilkinson et al. | |
| 4,157,378 A | 6/1979 | Tomlinson et al. | |

(Continued)

FOREIGN PATENT DOCUMENTS

EP 0 268 463 5/1988

(Continued)

OTHER PUBLICATIONS

Aggerbeck and Heron, "Adjuvanticity of Aluminum Hydroxide and Calcium Phosphate in Diptheria-Tetanus Vaccines I," *Vaccine* 13:1360-1365 (1995).

(Continued)

*Primary Examiner* — Carlos Azpuru
(74) *Attorney, Agent, or Firm* — Clark & Elbing LLP; Todd Armstrong

(57) ABSTRACT

Osteogenic bone implant compositions that approximate the chemical composition of natural bone are provided. The organic component of these implant compositions is osteoinductive despite the presence of the inorganic component and, further, is present in an amount sufficient to maximize the regenerative capabilities of the implant without compromising its formability and mechanical strength. The composition may be an osteoinductive powder, including demineralized bone matrix (DBM) particles, a calcium phosphate powder, and, optionally, a biocompatible cohesiveness agent. The powder may be combined with a physiologically-acceptable fluid to produce a formable, osteoinductive paste that self-hardens to form a poorly crystalline apatitic (PCA) calcium phosphate having significant compressive strength. The bone implant materials retain their cohesiveness when introduced at an implant site and are remodeled into bone in vivo. Methods for using these implant materials to repair damaged bone and a method of assaying the content of DBM particles, by weight, in a bone implant material are also provided.

94 Claims, 1 Drawing Sheet

U.S. PATENT DOCUMENTS

| | | | |
|---|---|---|---|
| 4,329,332 A | 5/1982 | Couvreur et al. |
| 4,346,709 A | 8/1982 | Schmitt |
| 4,347,234 A | 8/1982 | Wahlig et al. |
| 4,353,888 A | 10/1982 | Sefton |
| 4,429,691 A | 2/1984 | Niwa et al. |
| 4,609,327 A | 9/1986 | Nishimori |
| 4,612,053 A | 9/1986 | Brown et al. |
| 4,620,327 A | 11/1986 | Caplan et al. |
| 4,684,673 A | 8/1987 | Adachi |
| 4,737,411 A | 4/1988 | Graves, Jr. et al. |
| 4,842,603 A | 6/1989 | Draenert |
| 4,849,193 A | 7/1989 | Palmer et al. |
| 4,880,610 A | 11/1989 | Constantz |
| 4,892,538 A | 1/1990 | Aebischer et al. |
| RE33,161 E | 2/1990 | Brown et al. |
| 4,917,702 A | 4/1990 | Scheicher et al. |
| RE33,221 E | 5/1990 | Brown et al. |
| 4,938,938 A | 7/1990 | Ewers et al. |
| 4,959,104 A | 9/1990 | Iino et al. |
| 5,007,930 A | 4/1991 | Dorman et al. |
| 5,034,059 A | 7/1991 | Constantz |
| 5,037,639 A | 8/1991 | Tung |
| 5,041,138 A | 8/1991 | Vacanti et al. |
| 5,047,031 A | 9/1991 | Constantz |
| 5,053,212 A | 10/1991 | Constantz et al. |
| 5,073,373 A | 12/1991 | O'Leary et al. |
| 5,085,861 A | 2/1992 | Gerhart et al. |
| 5,129,905 A | 7/1992 | Constantz |
| 5,149,368 A | 9/1992 | Liu et al. |
| 5,152,836 A | 10/1992 | Hirano et al. |
| 5,178,845 A | 1/1993 | Constantz et al. |
| 5,197,985 A | 3/1993 | Caplan et al. |
| 5,226,914 A | 7/1993 | Caplan et al. |
| 5,258,044 A | 11/1993 | Lee |
| 5,262,166 A | 11/1993 | Liu et al. |
| 5,281,265 A | 1/1994 | Liu |
| 5,286,763 A | 2/1994 | Gerhart et al. |
| 5,290,558 A | 3/1994 | O'Leary et al. |
| 5,306,305 A | 4/1994 | Lee |
| 5,336,264 A | 8/1994 | Constanz et al. |
| 5,342,441 A | 8/1994 | Mandai et al. |
| 5,352,715 A | 10/1994 | Wallace et al. |
| 5,399,665 A | 3/1995 | Barrera et al. |
| 5,443,832 A | 8/1995 | Amerongen et al. |
| 5,462,751 A | 10/1995 | Kossovsky et al. |
| 5,470,803 A | 11/1995 | Bonfield et al. |
| 5,486,359 A | 1/1996 | Caplan et al. |
| 5,496,399 A | 3/1996 | Ison et al. |
| 5,508,342 A | 4/1996 | Antonucci et al. |
| 5,510,396 A | 4/1996 | Prewett et al. |
| 5,514,378 A | 5/1996 | Mikos et al. |
| 5,516,532 A | 5/1996 | Atala et al. |
| 5,522,893 A | 6/1996 | Chow et al. |
| 5,525,148 A | 6/1996 | Chow et al. |
| 5,542,973 A | 8/1996 | Chow et al. |
| 5,543,019 A | 8/1996 | Lee et al. |
| 5,545,254 A | 8/1996 | Chow et al. |
| 5,565,502 A | 10/1996 | Glimcher et al. |
| 5,569,442 A | 10/1996 | Fulmer et al. |
| 5,571,493 A | 11/1996 | Fulmer et al. |
| 5,580,623 A | 12/1996 | Fulmer et al. |
| 5,605,713 A | 2/1997 | Boltong |
| 5,650,176 A | 7/1997 | Lee et al. |
| 5,665,120 A | 9/1997 | Ohtsuka et al. |
| 5,676,976 A | 10/1997 | Lee et al. |
| 5,683,461 A | 11/1997 | Lee et al. |
| 5,683,496 A | 11/1997 | Ison et al. |
| 5,683,667 A | 11/1997 | Fulmer et al. |
| 5,691,397 A | 11/1997 | Glimcher et al. |
| 5,697,981 A | 12/1997 | Ison et al. |
| 5,700,289 A | 12/1997 | Breitbart et al. |
| 5,702,717 A | 12/1997 | Cha et al. |
| 5,709,742 A | 1/1998 | Fulmer et al. |
| 5,763,092 A | 6/1998 | Lee et al. |
| 5,782,971 A | 7/1998 | Constantz et al. |
| 5,783,217 A | 7/1998 | Lee et al. |
| 5,795,330 A | 8/1998 | Tofighi et al. |
| 5,820,632 A | 10/1998 | Constantz et al. |
| 5,843,289 A | 12/1998 | Lee et al. |
| 5,846,312 A | 12/1998 | Ison et al. |
| 5,885,540 A | 3/1999 | Fulmer et al. |
| 5,900,254 A | 5/1999 | Constantz |
| 5,904,716 A | 5/1999 | Gendler |
| 5,952,010 A | 9/1999 | Constantz |
| 5,958,504 A | 9/1999 | Lee et al. |
| 5,962,028 A | 10/1999 | Constantz |
| 5,964,932 A | 10/1999 | Ison et al. |
| 5,968,253 A | 10/1999 | Poser et al. |
| 5,980,482 A | 11/1999 | Tofighi et al. |
| 6,002,065 A | 12/1999 | Constantz et al. |
| 6,005,162 A | 12/1999 | Constantz |
| 6,027,742 A | 2/2000 | Lee et al. |
| 6,030,635 A | 2/2000 | Gertzman et al. |
| 6,033,582 A | 3/2000 | Lee et al. |
| 6,053,970 A | 4/2000 | Ison et al. |
| 6,071,982 A | 6/2000 | Wise et al. |
| 6,117,456 A | 9/2000 | Lee et al. |
| 6,132,463 A | 10/2000 | Lee et al. |
| 6,139,578 A | 10/2000 | Lee et al. |
| 6,214,368 B1 | 4/2001 | Lee et al. |
| 6,277,151 B1 | 8/2001 | Lee et al. |
| 6,287,341 B1 | 9/2001 | Lee et al. |
| 6,331,312 B1 | 12/2001 | Lee et al. |
| 6,334,891 B1 | 1/2002 | Constantz et al. |
| 6,340,477 B1 | 1/2002 | Anderson |
| 6,443,988 B2 | 9/2002 | Felt et al. |
| 6,461,631 B1 | 10/2002 | Dunn et al. |
| 6,464,889 B1 | 10/2002 | Lee et al. |
| 6,541,037 B1 | 4/2003 | Lee et al. |
| 6,544,290 B1 | 4/2003 | Lee et al. |
| 6,582,470 B1 | 6/2003 | Lee et al. |
| 6,599,516 B1 | 7/2003 | Knaack |
| 6,840,961 B2 | 1/2005 | Tofighi et al. |
| 6,953,594 B2 | 10/2005 | Lee et al. |
| 6,972,130 B1 | 12/2005 | Lee et al. |
| 7,318,841 B2 | 1/2008 | Tofighi et al. |
| 7,517,539 B1 | 4/2009 | Lee et al. |
| 2002/0076429 A1 | 6/2002 | Wironen et al. |
| 2002/0098222 A1 | 7/2002 | Wironen et al. |
| 2002/0136696 A1 | 9/2002 | Lee et al. |
| 2002/0155137 A1 | 10/2002 | Lee et al. |
| 2002/0155167 A1 | 10/2002 | Lee et al. |
| 2002/0187104 A1 | 12/2002 | Li et al. |
| 2002/0192263 A1 | 12/2002 | Merboth et al. |
| 2002/0193883 A1 | 12/2002 | Wironen |
| 2003/0049326 A1 | 3/2003 | Nimni et al. |
| 2003/0049329 A1* | 3/2003 | Lee et al. ............ 424/602 |
| 2003/0082232 A1 | 5/2003 | Lee et al. |
| 2003/0120351 A1 | 6/2003 | Tofighi et al. |
| 2004/0002558 A1 | 1/2004 | McKay |
| 2004/0097612 A1 | 5/2004 | Rosenberg et al. |
| 2005/0106260 A1 | 5/2005 | Constantz et al. |
| 2005/0147551 A1 | 7/2005 | Tofighi et al. |
| 2005/0260278 A1 | 11/2005 | Constantz et al. |
| 2005/0260279 A1 | 11/2005 | Constantz et al. |
| 2006/0018974 A1 | 1/2006 | Constantz et al. |
| 2006/0240121 A1 | 10/2006 | Lee et al. |

FOREIGN PATENT DOCUMENTS

| | | |
|---|---|---|
| EP | 0 347 028 | 12/1989 |
| EP | 0 419 275 | 3/1991 |
| EP | 0 664 133 | 7/1995 |
| JP | 63111875 | 5/1988 |
| JP | 63170205 | 7/1988 |
| JP | 2182261 | 7/1990 |
| JP | 5305134 | 11/1993 |
| JP | 6228011 | 8/1994 |
| JP | A H07-246235 | 9/1995 |
| JP | 7277712 | 10/1995 |
| JP | T-2002-501786 | 1/1998 |
| JP | A H10-151188 | 6/1998 |
| JP | T H-11-511722 | 10/1999 |
| JP | T 2000-500110 | 1/2000 |
| WO | WO 92/00109 | 1/1992 |
| WO | WO 92/02453 | 2/1992 |
| WO | WO 93/14718 | 8/1993 |
| WO | WO 94/02412 | 2/1994 |

| WO | WO 94/04657 | 3/1994 |
| WO | WO 94/08458 | 4/1994 |
| WO | WO 94/20064 | 9/1994 |
| WO | WO 94/25080 | 11/1994 |
| WO | WO 94/25637 | 11/1994 |
| WO | WO 95/08319 | 3/1995 |
| WO | WO 96/03160 | 2/1996 |
| WO | WO 96/36562 | 11/1996 |
| WO | WO 97/17285 | 5/1997 |
| WO | WO 98/15314 | 4/1998 |
| WO | WO 98/16209 | 4/1998 |
| WO | WO 98/16268 | 4/1998 |
| WO | WO99/38543 | 8/1999 |
| WO | WO 99/38543 | 8/1999 |
| WO | WO 01/08714 | 2/2001 |
| WO | WO 02/28332 | 4/2002 |
| WO | WO 02/41844 | 5/2002 |
| WO | WO 02/065981 | 8/2002 |
| WO | WO 03/057086 | 7/2003 |
| WO | WO 03/057137 | 7/2003 |
| WO | WO 2004/045372 | 6/2004 |
| WO | WO 2005/117919 | 12/2005 |
| WO | WO 2007/067561 | 6/2007 |
| WO | WO 2009/032173 | 3/2009 |

OTHER PUBLICATIONS

Alper et al. "Osteogenesis in Bone Defects in Rats: The Effects of Hydroxyapatite and Demineralized Bone Matrix," *Am. J. Med. Sci.* 298:371-376 (1989).
Aoki, "Science and Medical Applications of Hydroxyapatite," *JAAS* 11-15 (1991).
Appel et al., "Recent Advances in Implants for Bone Growth Promotion," *Exp. Opin. Ther. Patents* 4:1461-1469 (1994).
Atala et al., "Injectable Alginate Seeded with Chondrocytes as a Potential Treatment for Vesicoureteral Reflux," *J. Urol.* 150:745-747 (1993).
Athanasou, "Cellular Biology of Bone-Resorbing Cells," *J. Bone Joint Surg. Am.* 78:1096-1112 (1996).
Attawia et al., "Osteoblast-Like Cell Adherence and Migration Through 3-Dimensional Porous Polymer Matrices," *Biochem. Biophys. Res. Commun.* 213:639-644(1995).
Barton et al., "Surface and Bulk Properties of Amorphous Calcium Phosphate," *Surface Chem. Colloids* 87: 379 No. 73954v (1977).
Benghuzzi et al., "Alcap Ceramic Implantable Devices and the Effect of Surface Area on the Delivery of Various Steroid Hormones," 8th Southern Biomedical Engineering Conference, Richmond, VA, Oct. 15-16, 1989; Biomater. Artif. Cells Artif. Organs, 17:463 (1989).
Benghuzzi et al., "Long-Term Delivery of Danazol by Biodegradable Ceramic Devices," 8th Southern Biomedical Engineering Conference, Richmond, VA, Oct. 15-16, 1989; Biomater. Artif. Cells Artif. Organs, 17:463 (1989).
Benghuzzi et al., "Resorbable and Biodegradable Ceramics as Drug Delivery Systems," 8th Southern Biomedical Engineering Conference, Richmond, VA, Oct. 15-16, 1989; Biomater. Artif. Cells. Artif. Organs, 17:463 (1989).
Benghuzzi et al., "Controlled Release of Hydrophilic Compounds by Resorbable and Biodegradable Ceramic Drug Delivery Devices," *Biomed. Sci. Instrum.* 28:179-182 (1992).
Besic et al., "Electron Probe Microanalysis of Noncarious Enamel and Dentin and Calcified Tissues in Mottled Teeth," *J. Dent. Res.* 48:131-139 (1969).
Bonfield, "Chapter 16—Design of Bioactive Ceramic-Polymer Composites," An Introduction to Biometrics, IRC in Biomedical Materials, Queen Mary and Westfield College, London, UK, 16:299-303.
Boskey, "Matrix Proteins and Mineralization: An Overview," *Connect. Tissue Res.* 35:357-363 (1996).
Brown, "Phase Relationships in the Ternary System $CaO$-$P_2O_5$-$H_2O$ at 25 ° C.," *J. Am. Ceram. Soc.* 75:17-22 (1992).
Cannon et al., "Continuous Delivery of Azidothymidine by Hydroxyapatite or Tricalcium Phosphate Ceramics," *Biomed. Sci. Instrum.* 31:159-164 (1995).

Chung et al., "Biological Effects of Drug-Loaded Biodegradable Membranes for Guided Bone Regeneration," J. Periodont. Res . 32:172-175 (1997).
Constantz et al., "Skeletal Repair by in Situ Formation of the Mineral Phase of Bone," *Science* 267:1796-1799 (1995).
Covey et al., "Clinical Induction of Bone Repair with Demineralized Bone Matrix or a Bone Morphogenetic Protein," *Orthop. Rev.* 18:857-863 (1989).
Denissen et al., "Net-Shaped Hydroxyapatite Implants for Release of Agents Modulating Periodontal-Like Tissues," *J. Periodontal Res.* 32:40-46(1997).
Driessens et al., "Calcium Phosphate Bone Cements," *Encyc. Hand. Biomat. Bioeng.*, pp. 855-877 (1995).
Ducheyne et al., "Chapter 15: Bioceramic Composites," In *Advanced Series in Ceramics*—vol. 1: *An Introduction to Bioceramics*, 281-297 (1993).
Eanes et al., "Intermediate States in the Precipitation of Hydroxyapatite," *Nature* 208:365-367 (1965).
Eanes et al. "Intermediate Phases in the Basic Solution Preparation of Alkaline Earth Phosphates," *Chemical Abstracts* 69:10348, No. 110373f (1968).
Eanes, "Thermochemical Studies on Amorphous Calcium Phosphate," *Calcif. Tissue Res.* 5:133-145 (1970).
Elgendy et al., "Osteoblast-Like Cell (MC3T3-E1) Proliferation on Bioerodible Polymers: An Approach Towards the Development of a Bone-BioErodible Polymer Composite Material," *Biomater.* 14:263-269 (1993).
Fabbri et al., "Hydroxyapatite-Based Porous Aggregates: Physico-Chemical Nature, Structure, Texture and Architecture," *Biomater.* 16: 225-228 (1995).
Fink and Simonsmeier, "Business Laws," *Rem. Pharm. Sci. 17Ed.* 1890-1891 (1985).
Freed et al., "Cultivation of Cell-Polymer Cartilage Implants in Bioreactors," *J. Cellular Biochemistry* 51:257-264 (1993).
Freed et al., "Biodegradable Polymer Scaffolds for Tissue Engineering," *Biotech.* 12:689-693 (1994).
Gennaro, ed., "Clinical/ Medical Testing," *Rem. Pharm. Sci. 17$^{th}$ Ed.* 39-40 (1985).
Glimcher et al., "Recent Studies of Bone Mineral: Is the Amorphous Calcium Phosphate Theory Valid," *J. Crystal Growth* 53:100-119 (1981).
Glimcher, "Recent Studies of the Mineral Phase in Bone and its Possible Linkage to the Organic Matrix by Protein-Bound Phosphate Bonds," *Philos. Trans. R. Soc. Lond. B.* 304:479-508 (1984).
Glowacki et al., "Demineralized Bone Implants," *Clin. Plast. Surg.* 12:233-241 (1985).
Goto et al., "Studies on the Toxicities of Aluminum Hydroxide and Calcium Phosphate as Immunological Adjuvants for Vaccines," *Vaccine* 11:914-918 (1993).
Goto et al., "Local Tissue Irritating Effects and Adjuvant Activities of Calcium Phosphate and Aluminum Hydroxide with Different Physical Properties," *Vaccine* 15:1364-1371 (1997).
Graves et al., "Resorbable Ceramic Implants," *J. Biomed. Mater. Res. Symposium* 2:91-115 (1971).
Greenfield et al., "Formation Chemistry of Amorphous Calcium Phosphates Prepared from Carbonate Containing Solutions," *Calc. Tiss. Res.* 9:152-162 (1972).
Gupta et al., "Adjuvants—A Balance Between Toxicity and Adjuvanticity," *Vaccine* 11:293-306 (1993).
Gupta et al., "Comparison of Adjuvant Activities of Aluminum Phosphate, Calcium Phosphate and Stearyl Tyrosine for Tetanus Toxoid," *Biologicals* 22:53-63 (1994).
Hirasawa et al., "Manufacture of High Purity Hydroxyapatite," *Chemical Abstracts*, 108:166-167, No. 78193h (1988).
Holmes et al., "Surface Areas by Gas Adsorption on Amorphous Calcium Phosphate and Crystalline Hydroxyapatite," *Calc. Tiss. Res.* 7:163-174 (1971).
Hubbell, "Biomaterials in Tissue Engineering," *Biotech.* 13:565-576 (1995).
Ickovic et al., "Calcium-Phosphate-Adjuvanted Allergens: Total and Specific IgE Levels Before and After Immunotherapy with House Dust and *Dermatophagoides pteronyssinus* Extracts," *Ann. Immunol.* 134D:385-398 (1983).

IJntema et al., "Hydroxyapatite Microcarriers for Biocontrolled Release of Protein Drugs," *Int'l. J. Pharm.* 112:215-224 (1994).
Ikada et al., "Release of Antibiotic from Composites of Hydroxyapatite and Poly(lactic acid)," *J. Control. Release* 2:179-186 (1985).
Ishaug et al., "Osteoblast Function on Synthetic Biodegradable Polymers," *J. Biomed. Mater. Res.* 28:1445-1453 (1994).
Ishikawa et al., "Effects of Preparation Conditions in Aqueous Solution on Properties of Hydroxyapatites," *Chemical Abstracts*, 113: 6001, No. 218168 (1990).
Itokazu et al., "Drug Delivery Systems Using Porous Hydroxyapatite Blocks," *J. Orthop. Surg.* 2:47-50 (1994).
Kato et al., "Relationship Between Hemolytic Activity and Adsorption Capacity of Aluminum Hydroxide and Calcium Phosphate as Immunological Adjuvants for Biologicals," *Microbiol. Immunol.* 38:543-548 (1994).
Knaack et al., "Novel Fully Resorbable Calcium Phosphate Bone Substitute," *1997 ASBMR Abstract*, 12: s202, (1997).
Knaack, "Endothermically Setting Calcium Phosphate Bone Substitute," Orthopaedic Congress, Aug. 20-22, 1997, Boston, MA.
Knaack et al., "A Fully Resorbable Calcium Phosphate Bone Substitute," Portland Bone Symposium, pp. 692-701, (1997).
Kossovsky et al., "Surface-Modified Nanocrystalline Ceramics for Drug Delivery Applications," *Biomaterials* 15:1201-1207 (1994).
Kossovsky et al., "Preservation of Surface-Dependent Properties of Viral Antigens Following Immobilization on Particulate Ceramic Delivery Vehicles," *J. Biomed. Mat. Res.* 29:561-573 (1995).
Kreuter et al., "Influence of the Particle Size on the Adjuvant Effect of Particulate Polymeric Adjuvants," *Vaccine* 4:125-129 (1986).
Labarthe et al., "Sur la Structure et les Propriétés des Apatites Carbonatées de Type B Phospho-Calciques," *Ann. Chem.* 8:289-301 (1973).
Mileti et al., "Development of a Hydroxyapatite Ceramic Matrix for the Continuous Delivery of Coumadin," *Biomed. Sci. Instrum.* 31:177-182 (1995).
Moldovan et al., "A Ceramic System for Continuous Release of Acetylsalicylic Acid," *Biomed. Sci. Instrum.* 30:175-180 (1994).
Moldovan et al., "Continuous Delivery of Analgesics by Ceramics," Fifth World Biomaterials Congress, Toronto, Canada, Jun. 2, 1996.
Norian Corporation, Product Information Sheet, "The Material Science of Norian SRS™, Skeletal Repair System™," (1997).
Nylen et al, "Molecular and Ultrastructural Studies of Non-Crystalline Calcium Phosphates," *Calcif. Tissue Res.* 9:95-108 (1972).
Otsuka et al., "Drug Release Behavior from Self-Setting Calcium Phosphate Cement Containing Anti-Cancer Drug," *Proceed. Intern. Symp. Control. Rel. Bioact. Mater.* 21:268-269 (1994).
Otsuka et al., "A Novel Skeletal Drug Delivery System Using Self-Setting Calcium Phosphate Cement. 4: Effects of the Mixing Solution Volume on the Drug Release Rate of Heterogenous Aspirin-Loaded Cement," *J. Pharm. Sci.* 83:259-263 (1994).
Otsuka et al., "A Novel Skeletal Drug Delivery System Using Self-Setting Calcium Phosphate Cement. 9: Effects of the Mixing Solution Volume on Anticancer Drug Release from Homogeneous Drug-Loaded Cement," *J. Pharm. Sci.* 84:733-736 (1995).
Otsuka et al., "Effect of Particle Size of Metastable Calcium Phosphates on Mechanical Strength of a Novel Self-Setting Bioactive Calcium Phosphate Cement," *J. Biomed. Mater. Res.* 29:25-32 (1995).
Pool, "Coral Chemistry Leads to Human Bone Repair," *Science* 267:1772 (1995).
Posner et al., "Synthetic Amorphous Calcium Phosphate and its Relation to Bone Mineral Structure," *Bone Mineral Structure*, 8: 273-281 (1975).
Redondo et al., "Effect of particulate porous hydroxyapatite on osteoinduction of demineralized bone autografts in experimental reconstruction of the rat mandible," *Int. J. Oral. Maxillofac. Surg.* 24:445-448 (1995).
Relyveld, "Current Developments in Production and Testing of Tetanus and Diptheria Vaccines," *New Developments with Human and Veterinary Vaccines*, pp. 51-76 (1980).
Relyveld et al., "Calcium Phosphate Adjuvanted Allergens," *Annals of Allergy* 54:521-529 (1985).
Relyveld et al., "Preparation and Use of Calcium Phosphate Adsorbed Vaccines," *Develop. Biol. Standard* 65:131-136 (1986).
Relyveld et al, "Humoral Response in Rabbits Immunized with Calcium Phosphate Adjuvanted HIV-1 gp160 Antigen," *Biomed. & Pharmacother.* 48:79-83 (1994).
Rey et al., "The Carbonate Environment in Bone Mineral: A Resolution-Enhanced Fourier Transform Infrared Spectroscopy Study," *Calcif. Tissue Int.* 45:157-164 (1989).
Rey et al., "Structural Studies of the Mineral Phase of Calcifying Cartilage," *J. Bone Miner. Res.* 6:515-525 (1991).
Rey et al., "Preparation of Microporous Ceramic at Low Temperature from Poorly Crystalline Apatite," *Symposium V: Hydroxyapatite and related compounds* (1993).
Rey et al., "Chemical Properties of Poorly Crystalline Apatites" *Phosphorus Res. Bull*, 6:67-70 (1996).
Shinto et al., "Calcium Hydroxyapatite Ceramic Used as a Delivery System for Antibiotics," *J. Bone Joint Surg. Br*. 74-B:600-604 (1992).
Shors et al., "Chapter 10: Porous Hydroxyapatite," In *An Introduction to Bioceramics*, eds. Hersch et al., Work Sci. Publ. Co. Pte. Ltd.: 181-198 (1993).
Termine et al., "Amorphous/Crystalline Interrelationships in Bone Mineral," *Calc. Tissue Res.* 1: 8-23 (1967).
Thoma et al., "Biodegradable Gentamicin Depot-Implants Made of Beta-Tricalcium Phosphate Ceramics. 3: In Vivo Studies on Drug Release, Tissue Tolerance, and Biodegradation," *Pharmazie* 46:266-270 (1991).
Thoma et al., "Biodegradable Controlled Release Implants Based on β-Tricalcium Phosphate Ceramic," *Eur. J. Pharm. Biopharm.* 38:107-112 (1992).
Thomson et al., "Fabrication of Biodegradable Polymer Scaffolds to Engineer Trabecular Bone," *J. Biomater. Sci. Polym. Edn.* 7:23-30 (1995).
Törmälä, "Biodegradable Self-Reinforced Composite Materials; Manufacturing Structure and Mechanical Properties," *Clin. Mater.* 10:29-34 (1992).
Tung et al., "An Intermediate State in Hydrolysis of Amorphous Calcium Phosphate," *Calcif. Tissue Int.* 35:783-790 (1983).
Tung, "In Vitro Drug Release of Antibiotic-Loaded Porous Hydroxyapatite Cement," *Artif. Cells Blood Substit. Immob. Biotech.* 23:81-88 (1995).
Uchida et al., "Slow Release of Anticancer Drugs from Porous Calcium Hydroxyapatite Ceramic," *J. Orthop. Res.* 10:440-445 (1992).
Vassilev, "Aluminium Phosphate But Not Calcium Phosphate Stimulates the Specific IgE Response in Guinea Pigs to Tetanus Toxoid," *Allergy* 33:155-159 (1978).
Yamamura et al., "Antitumor Effects and Distrubutions of Adriamycin Incorporated Into Hydroxyapatite Implants in a Cancer Rat Model Bearing Swarm Rat Chondrosarcoma," *Japan. J. Pharm.* 66:433-438 (1994).
Yamamura et al., "Anticancer Effects of Adriamycin-Loaded Hydroxyapatite Implants Determined in a Swarm Rat Chondrosarcoma Model," *Japan. J. Pharm.* 65:289-291 (1994).
Yasue et al., "Effect of Adsorption of Succinic Acid on the Formation of Amorphous Calcium Phosphate," *J. Ceramic Soc. Japan* (International Edition), 102: 1125-1130 (1994).
Supplementary European Search Report issued in EP 04759427 on Nov. 30, 2009.
Examiner's Report for Australian Application No. 2004229502 dated Feb. 2, 2009.
Communication Pursuant to Article 94(3) EPC for European Application No. 04 759 427.0 dated Mar. 30, 2010.
Notice of Reasons for Rejection for Japanese Application No. 2006-509917 dated Nov. 17, 2010.
Korean Office Action for Korean Application No. 10-2005-7019292 dated Feb. 20, 2011.
European Patent Office Communication (EP 04 759 427.0) dated Apr. 17, 2012.

* cited by examiner

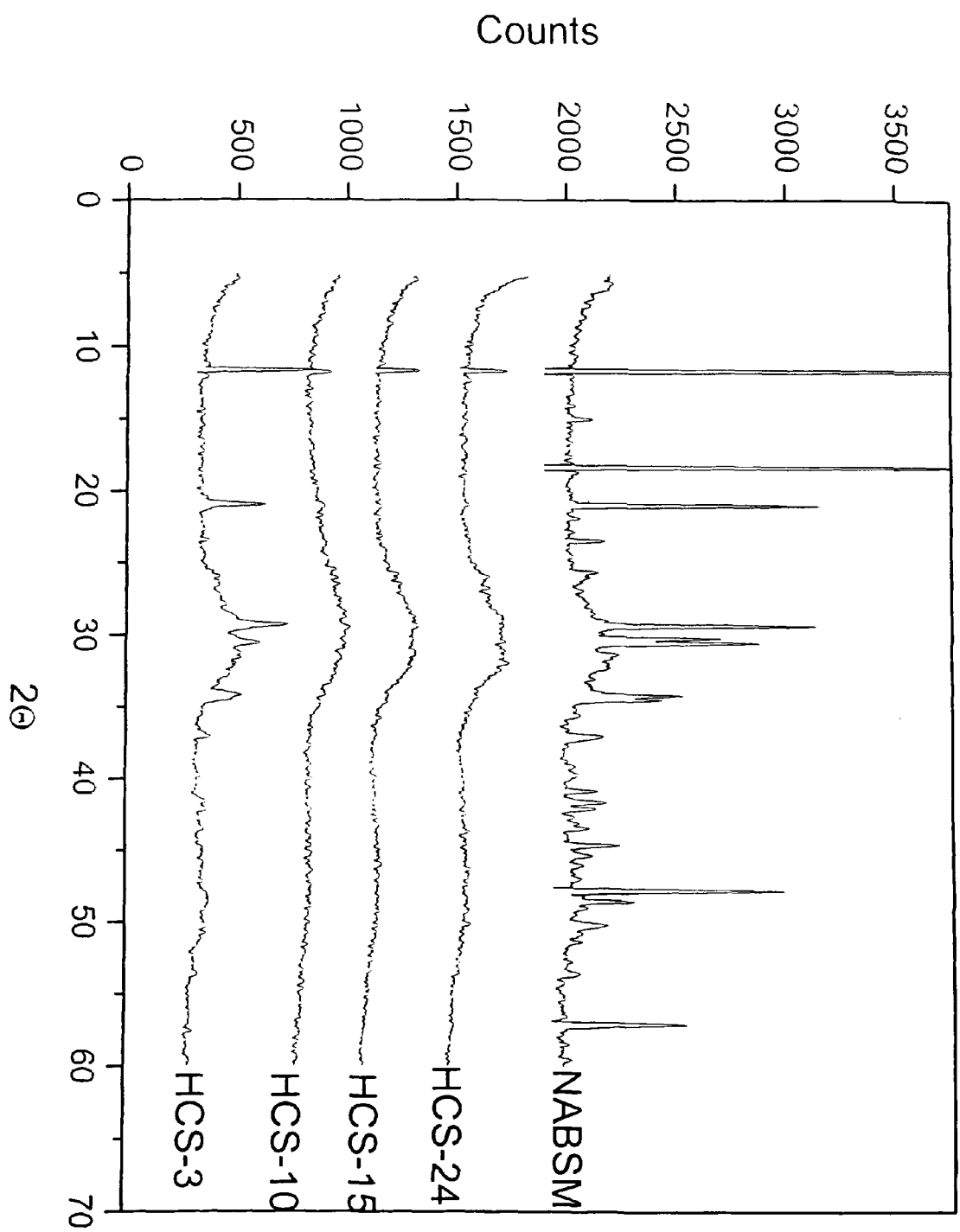

US 8,221,781 B2

OSTEOINDUCTIVE BONE MATERIAL

CROSS REFERENCE TO RELATED APPLICATIONS

This application claims the benefit of the filing date of U.S. Provisional Application No. 60/462,416, filed on Apr. 11, 2003, which is incorporated herein by reference.

BACKGROUND OF THE INVENTION

The field of the present invention is bone repair and replacement. More specifically, the invention relates to a self-hardening, osteogenic composition, which has desirable handling characteristics and mechanical properties.

Naturally-occurring bone is comprised of both organic and inorganic components. The organic component includes growth factors, cartilage, collagen, and other proteins. The inorganic bone component includes non-stoichiometric, poorly crystalline apatitic (PCA) calcium phosphate, having a Ca/P ratio between 1.45 and 1.75 (Besic et al. (1969) *J. Dental Res.* 48 (1): 131). This inorganic bone mineral is continuously resorbed and regenerated in vivo by osteoclasts and osteoblasts.

Bone implants are often used to augment the natural regeneration process in the event of bone defects and injuries. These implants must be biocompatible. Additionally, an ideal bone implant should be osteogenic, i.e., both osteoconductive and osteoinductive, easily manipulated by a surgeon prior to implantation, and of a strength and composition such that the implant will maintain its shape in vivo.

Given its regenerative capabilities, natural bone is a potential implant material. However, the use of autogenic, allogenic, and xenogeneic bone is complicated by associated disease transmission, immunogenic implant rejection, patient morbidity, and complicated surgical procedures. Thus, synthetic bone implant materials have become the focus of increasing attention.

Metal implant devices have been and continue to be used because of their high strength and stability. Despite these advantages, metal devices are disfavored because they cannot be resorbed into natural bone mineral and are, consequently, permanent foreign bodies once implanted.

To overcome the deficiencies of metal implants, compositions more closely approximating natural bone have been developed. Organic, osteoinductive materials are desirable components of such compositions. Commonly used osteoinductive materials include demineralized bone matrix (DBM) and recombinant human bone morphogenic proteins (rh-BMPs; see, e.g., U.S. Pat. No. 6,030,635; European Patent Appln. No. 0 419 275; PCT/US00/03024; PCT/US99/01677; and PCT/US98/04904). These organic, osteoinductive materials are typically delivered to in implant site in combination with a fluid or gelatinous carrier (see, e.g., U.S. Pat. No. 6,030,635; U.S. Pat. No. 5,290,558; U.S. Pat. No. 5,073,373; and PCT/US98/04904). An ideal bone implant includes substantial quantities of these osteoinductive materials so as to maximize its regenerative capabilities.

These organic, osteoinductive materials have previously been combined with hydroxyapatite and/or tricalcium phosphate to form synthetic bone compositions. The utility of these synthetic bone implants is offset by the tendency of the hydroxyapatite and/or tricalcium phosphate to inhibit the osteoinductivity of the organic component (see, e.g., Redondo, L. M. et al. (1995) *Int. J. Oral Maxillofac. Surg.* 24 (6):445-448; Lindholm, T. C. et al. (1993) *Ann. Chir. Gynaecol. Suppl.* 207:91-98; Alper, G. et al. (1989) *Am. J. Med. Sci.* 298 (6):371-376). More recently, organic, osteoinductive materials have been combined with resorbable calcium phosphate compositions, such as those including amorphous calcium phosphate and poorly crystalline apatitic (PCA) calcium phosphate (see, e.g., U.S. Pat. No. 6,027,742; PCT/US00/20630; and PCT/US00/03024). The mechanical strength of these implants, though, diminishes as larger quantities of the osteoinductive component (e.g., DBM) are incorporated. Furthermore, implants containing desirable amounts of osteoinductive materials tend to be difficult to manipulate and to lose their cohesiveness and shape in vivo. Therefore, there is a need for improved bone implant materials containing a calcium phosphate component and DBM particles that have a high compressive strength.

SUMMARY OF THE INVENTION

Osteogenic bone implant compositions are provided that approximate the chemical composition of natural bone. The organic component of these implant compositions is osteoinductive despite the presence of the inorganic component and, further, is present in an amount sufficient to maximize the implant's regenerative capabilities without compromising its formability and mechanical strength.

In one aspect, the composition is an osteoinductive powder including demineralized bone matrix (DBM) particles, a calcium phosphate powder, and, optionally, a biocompatible cohesiveness agent (e.g., a binder). The DBM particles may be of various sizes and shapes. In a preferred embodiment, the calcium phosphate powder includes an amorphous calcium phosphate and a second calcium phosphate source. In some embodiments, the amorphous calcium phosphate and the second calcium phosphate source have an average crystalline domain size of less than 100 nm. Such crystalline domain sizes may be obtained by, for example, high energy milling processes. In some embodiments, the second calcium phosphate source is an acidic calcium phosphate. In other embodiments, the osteogenic powder, upon hydration with a physiologically acceptable fluid, self-hardens to form a poorly-crystalline apatitic calcium phosphate. In yet other embodiments, the poorly-crystalline apatitic calcium phosphate has a Ca/P ratio of less than 1.67. A particularly preferred osteogenic powder includes demineralized bone matrix (DBM) particles, a combination of calcium phosphate powders, and, optionally, a biocompatible cohesiveness agent (e.g., a binder), in which the combination of calcium phosphate powders react, when admixed with a physiologically acceptable liquid, to for an apatitic calcium phosphate having an overall Ca/P ratio in the range of about 1.0 to about 1.67, preferably 1.3-1.65, more preferably 1.4-1.6, and most preferably close to that of naturally-occurring bone, that is in the range of 1.45 to 1.67. In other embodiments of the osteoinductive powder, the DBM particles are present in an amount of less than about 60 wt %, less than about 50 wt %, less than about 20 wt % (e.g., about 15 wt %), or the DBM particles are present in an amount in the range of about 1 to about 60 wt %. In yet other embodiments, the DBM particles have a particle size of less than about 850 μm (e.g., less than about 125 μm), for example, in the range of about 125 to about 850 μm or in the range of about 53 to about 125 μm.

In another aspect, the composition is a formable, self-hardening, poorly crystalline apatitic (PCA) calcium phosphate paste including an osteoconductive powder as described above and a physiologically-acceptable fluid. The paste is cohesive when applied to an implant site in vivo. In at least some embodiments, the paste hardens to form a poorly crystalline apatitic (PCA) calcium phosphate having significant strength. The composition may be implanted in vivo in paste form or as hardened PCA calcium phosphates to repair damaged bone. In other embodiments, the formable, self-hardening, osteoinductive paste hardens to form a poorly-crystalline apatitic calcium phosphate. In yet other embodiments, the poorly-crystalline apatitic calcium phosphate has a Ca/P ratio of less than 1.67. In particularly preferred embodiments, the formable, self-hardening, osteoinductive paste hardens to form an apatitic calcium phosphate having an overall Ca/P ratio in the range of 1.0-1.67, preferably 1.3-1.65, more preferably 1.4-1.6, and most preferably close to that of naturally-occurring bone, that is in the range of 1.45 to 1.67. In a preferred embodiment, the poorly-crystalline apatitic calcium phosphate has a Ca/P ratio of equal to or less than about 1.5.

In preferred embodiments, the formable, self-hardening, PCA calcium phosphate paste additionally includes a cohesiveness agent. Preferred cohesiveness agents include polymers selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof.

According to some embodiments, the composition additionally includes a biologically active agent. Biologically active agents that can be used in the compositions and methods described herein include, without limitation, an antibody, an antibiotic, a polynucleotide, a polypeptide, a protein (e.g., an osteogenic protein), an anti-cancer agent, a growth factor, and a vaccine. Osteogenic proteins include, without limitation, BMP-2, BMP-4, BMP-5, BMP-6, BMP-7, BMP-10, BMP-12, BMP-13, and BMP-14. Anti-cancer agents include, without limitation, alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists, TNF alpha antagonists, endothelin A receptor antagonists, retinoic acid receptor agonists, immuno-modulators, hormonal agents, antihormonal agents, photodynamic agents, and tyrosine kinase inhibitors.

The composition may optionally include an effervescent agent. An exemplary effervescent agent is sodium bicarbonate, carbon dioxide, air, nitrogen, helium, oxygen, and argon. The composition may include, for example, from about 1 to about 40 weight percent of an effervescent agent.

In yet another aspect, a method of assaying the amount of DBM, by weight, in a mixture including DBM and a calcium phosphate powder is provided.

We have observed that small size DBM particles of 53-125 μm (i.e., Fines) and full range DBM particles (e.g., of 125-850 μm) demonstrate significant bone induction when implanted without a carrier. We also observed that DBM fines tested in an ectopic (athymic rat) model induced more bone formation than did the full range DBM particles, while DBM fines tested without a carrier in a sheep interbody fusion model demonstrated 100% fusion rates. Commercial DBM suppliers and tissue banks supply DBM within the 125-180 μm range as a bone graft extender or replacement for orthopedic applications. DBM in the 53-125 μm range is not used for orthopedic applications. We believe that the use of 53-125 μm DBM is a novel approach to utilizing DBM for orthopedic applications.

As used herein, the term "about" means±10% of the recited value.

As used herein and applied to a calcium phosphate, the term "amorphous" means a calcium phosphate having no or only short range crystallographic order, i.e., crystallographic order over less than 100 mm.

As used herein and applied to a DBM particle, the term "aspect ratio" means the ratio of the longest dimension of the particle to the shortest dimension of the particle.

As used herein, a "biocompatible" substance is one that is non-toxic and does not provoke an undesirable physiological response, e.g., an immune response, in the recipient.

As used herein and applied to a composition, the term "cohesiveness" means the ability of the composition, when mixed with a biocompatible fluid, to maintain its shape without loss of mass. A composition is deemed cohesive if greater than 90% of its initial mass and volume are retained within its initial shape dimension in an aqueous environment for at least 10 minutes.

As used herein, a "cohesiveness agent" means an additive that, when included in a calcium phosphate composition of the invention, improves the ability of the calcium phosphate composition to maintain its cohesiveness. Preferred cohesiveness agents include polymers selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, α-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof.

As used herein, "poorly crystalline apatitic (PCA) calcium phosphate" means a synthetic calcium phosphate material having small crystalline domains, on the order of those found in naturally-occurring bone, and characterized by a broad, poorly-defined X-ray diffraction pattern and a Ca/P ratio of less than 1.67. The PCA calcium phosphate is not necessarily restricted to a single calcium phosphate phase, provided it demonstrates the characteristic X-ray diffraction pattern of an apatitic mineral, namely two broad peaks in the region of 20-35° with a peak centered at 26° and a second peak centered at 32°.

BRIEF DESCRIPTION OF THE DRAWINGS

The invention is described with reference to the following figures, which are presented for the purpose of illustration only and which are not intended to be limiting of the invention.

FIG. 1 illustrates the X-ray diffraction (XRD) pattern of a calcium phosphate powder comprising amorphous calcium phosphate and dicalcium phosphate dihydrate (DCPD) before high energy milling and after high energy milling for 3, 10, 15, and 24 hours in a high energy ball mill.

DETAILED DESCRIPTION OF THE INVENTION

Formable, self-hardening, osteogenic bone implant materials having a chemical composition comparable to that of natural bone, and which retain cohesiveness when introduced at an implant site in vivo, are provided. These bone implant materials are highly osteoinductive despite their chemical composition. Further, upon hardening, these implant materials display significant compressive strength.

The bone implant material includes demineralized bone matrix (DBM) particles. The DBM particles are mixed with a calcium phosphate powder, which includes an amorphous calcium phosphate and a second calcium phosphate source to form an osteoinductive powder. The osteoinductive powder may further include a biocompatible cohesiveness agent (e.g., a binder). Upon combination with a physiologically-acceptable fluid, the osteoinductive powder produces a formable paste that hardens and reacts to form a poorly-crystalline apatitic calcium phosphate. Preferably the poorly-crystalline apatitic calcium phosphate has a Ca/P ratio of less than 1.67. For example, the poorly-crystalline apatitic calcium phosphate desirably has an overall Ca/P ratio in the range of 1.0-1.67, preferably 1.3-1.65, more preferably 1.4-1.6, and most preferably in the range of 1.45 to 1.67 (i.e., close to that of naturally-occurring bone). Preferably, the poorly-crystalline apatitic calcium phosphate has a Ca/P ratio of about 1.5. This PCA calcium phosphate is remodeled into bone in vivo. The nature of the calcium phosphate powder and/or the presence of the biocompatible cohesiveness agent permit the inclusion of substantial quantities of DBM particles in the bone implant materials without compromising their formability or mechanical strength. Thus, the implant material retains its cohesiveness following implantation at an implant site in vivo and displays significant compressive strength upon hardening. Notably, in at least some embodiments, the implant material is highly osteoinductive despite the presence of the inorganic calcium phosphate sources.

DBM is an organic, osteoinductive material most commonly obtained from long bone chips demineralized by acid treatment. The acid treatment dissolves inorganic mineral components and acid-soluble proteins in the bone, leaving behind a collagen matrix as well as acid-insoluble proteins and growth factors (see, e.g., Glowacki et al. (1985) *Clin. Plast. Surg.* 12 (2):233-241; Covey et al. (1989) *Orthop. Rev.* 17 (8):857-863). Among the residual acid-insoluble proteins and growth factors are osteoinductive factors, such as bone morphogenic proteins (BMPs) and transforming growth factors (TGFs). Thus, DBM is osteoinductive, fully resorbable, and, when used in combination with the calcium phosphate powders described herein, yields bone implant materials that are highly biocompatible because they closely mimic the chemical composition of natural bone. Advantageously, DBM costs less than many other available organic bone composition additives, such as isolated BMPs.

The DBM employed in the bone implant materials is preferably derived from autogenic or allogenic sources. As discussed above, DBM may be obtained by acid treatment of long bone chips, a process well known to those of ordinary skill in the art. Alternatively, commercially-available DBM may be used (e.g., DBM available from Allosource, American Red Cross, Musculoskeletal Transplant Foundation, Regeneration Technologies, Inc., and Osteotech, Inc.).

In at least some embodiments, the DBM in the bone implant materials is present in an amount between about 10 and about 70 weight percent of the powder component. In particular embodiments, the DBM is present in an amount equal to about 60 weight percent of the powder component. In other embodiments, the DBM is present in an amount between about 1 and about 50 weight percent of the powder component. In still other embodiments, the DBM is present in an amount less than or equal to about 20 weight percent of the powder component. Preferably, the DBM is present in an amount less than or equal to about 15 weight percent of the powder component.

The amount of DBM in a given composition will vary depending upon the presence or absence of a biocompatible cohesiveness agent, as well as the intended use and desired characteristics of the bone implant material. In particular embodiments, the cohesiveness agent is present in the osteogenic powder in an amount in the range of about 0.5 and about 20 weight percent of the powder component. In preferred embodiments, the cohesiveness agent is present in an amount of about 5 weight percent or less.

Those of skill in the art will be able to determine the amount of DBM, calcium phosphate, and cohesiveness agent required for particular applications. For example, a preferred osteogenic powder composition includes about 15 weight percent DBM and about 85 weight percent calcium phosphate powder. Another preferred osetogenic powder includes about 50 weight percent DBM, about 45 weight percent calcium phosphate powder, and about 5 weight percent biocompatible cohesiveness agent.

The DBM particles may be of various sizes and physical forms. As with the amount of DBM, the size and form of the DBM particles will vary depending upon the intended use of the bone implant material. In some embodiments, the DBM particles have a longest dimension measuring between about 35 µm and about 850 µm and may further have an aspect ratio of less than about 5. In other embodiments, the DBM particles are fibrous in nature. In some embodiments, these DBM fibers have a length between about 50 μm and about 3 mm. In other embodiments, these DBM fibers have a length between about 250 μm and about 2 mm. In some embodiments, the aspect ratio of these DBM fibers is greater than 4. In other embodiments, the aspect ratio of these DBM fibers is greater than 10. The DBM fibers may be needle-like, having an average width to average thickness ratio of less than 5. Methods of producing DBM particles of varying sizes will be well-known to those of skill in the art and are disclosed, for example, in co-pending U.S. patent application Ser. No. 10/298,112, filed on Nov. 15, 2002, and entitled "Cohesive Demineralized Bone Compositions," which is incorporated herein by reference. Of note, the needle-like, fibrous DBM obtained from long bone chips or shavings, as opposed to DBM obtained from ground bone, provide increased cohesiveness when incorporated into the bone implant compositions of the present invention.

The incorporation of DBM into calcium phosphate-based bone implant materials has heretofore been limited, due to the tendency of DBM to reduce the mechanical strength of the implant materials into which it is incorporated. Thus, implant materials containing quantities of DBM necessary to maximize its osteoinductive capabilities are difficult to manipulate, lack formability, and lose their cohesiveness and shape following implantation in vivo. The hardened calcium phosphate product is also much weaker. Moreover, the effective use of DBM in bone implant materials containing inorganic, osteoconductive components, such as calcium phosphates, has been heretofore unsuccessful because the inorganic components inhibit the osteoinductivity of the DBM.

The bone implant materials described herein overcome these known deficiencies in several ways. According to some embodiments, the bone implant materials include a calcium phosphate powder having features that increase the mechanical strength of the implant. The calcium phosphate powder includes an amorphous calcium phosphate and a second calcium phosphate. Both the amorphous calcium phosphate and the second calcium phosphate have an average crystalline domain size of less than about 100 nm. This calcium phosphate powder, particularly when combined with a physiologically-acceptable fluid to form a self-hardening paste, provides formability and cohesiveness to implant materials containing substantial quantities of DBM. Moreover, the calcium phosphate powder does not inhibit the osteoinductivity of the DBM; in fact, certain formulations of the implant materials disclosed herein demonstrate superior osteoinductivity as compared to DBM alone. These advantages are largely attributable to the crystallinity, particle size, and reactivity of the calcium phosphate sources used to prepare the calcium phosphate powder. The selection of appropriate amounts, sizes, and shapes of DBM particles, as discussed herein, also contributes to these advantageous characteristics.

As mentioned above, the calcium phosphate powder includes an amorphous calcium phosphate and a second calcium phosphate source. Amorphous calcium phosphate has a broad, diffuse X-ray diffraction pattern, is homogenous when measured on an Angstrom scale, and is a gel-like material formed by rapid precipitation from a solution containing calcium and phosphate ion sources. The rapid precipitation creates numerous defects in the calcium phosphate nuclei. Under physiological conditions, amorphous calcium phosphate has a high solubility, high formation rate, and high rate of conversion to PCA calcium phosphate.

Amorphous calcium phosphate has a Ca/P molar ratio in the range of about 1.1 to about 1.9. In at least some embodiments of the instant invention, the amorphous calcium phosphate has a Ca/P molar ratio of less than 1.5. In particular embodiments, the Ca/P molar ratio is between about 1.35 and about 1.49. The Ca/P molar ratio of the amorphous calcium phosphate may be modified by the introduction of additional ions into the calcium and phosphate ion-containing solution. Non-limiting examples of such additional ions include $CO_3^{2-}$, $Mg^{2+}$, $P_2O_7^{4-}$, nitrate, nitrite, or acetate ions. The preparation and characterization of amorphous calcium phosphates are described further in U.S. Pat. Nos. 5,650,176 and 6,214,368, which are incorporated herein by reference.

In at least some embodiments, the amorphous calcium phosphate is present in an amount greater than or equal to about 20 wt % of the powder component. In particular embodiments, the amorphous calcium phosphate is present in an amount greater than or equal to about 30 wt % of the powder component.

A second calcium phosphate source is included in the calcium phosphate powder. The second calcium phosphate source may be crystalline or amorphous. Appropriate second calcium phosphate sources for use in the instant invention include acidic and neutral calcium phosphates having a stoichiometry such that they produce apatitic calcium phosphates upon reaction with amorphous calcium phosphate. Non-limiting examples of suitable acidic calcium phosphates include calcium metaphosphate, dicalcium phosphate dihydrate, heptacalcium phosphate, tricalcium phosphate, calcium pyrophosphate dihydrate, poorly crystalline hydroxyapatite, calcium pyrophosphate, and octacalcium phosphate. In particular embodiments, the second calcium phosphate source is dicalcium phosphate dihydrate (DCPD).

The amorphous calcium phosphate and the second calcium phosphate source should be selected such that they produce a calcium phosphate powder having a desired overall Ca/P molar ratio. Thus, the amorphous calcium phosphate and the second calcium phosphate source are used in proportions ranging from 1:10 to 10:1, or 1:5 to 5:1, or about 1:1. In at least some embodiments, the desired calcium phosphate product is poorly crystalline apatitic (PCA) calcium phosphate. Because the reaction forming PCA calcium phosphate from the amorphous calcium phosphate and the second calcium phosphate source proceeds substantially to completion, the Ca/P molar ratio of the amorphous calcium phosphate and the second calcium phosphate source should be equivalent to that of the product. PCA calcium phosphate has a Ca/P molar ratio between about 1.1 and about 1.9. Thus, according to at least some embodiments of the instant invention, the amorphous calcium phosphate and the second calcium phosphate source should have a Ca/P molar ratio between about 1.1 and about 1.9. In some embodiments, the Ca/P molar ratio of the amorphous calcium phosphate and the second calcium phosphate source ranges from about 1.1 to about 1.7. Preferably, the amorphous calcium phosphate and the second calcium phosphate source when combined forms a poorly crystalline apatitic (PCA) calcium phosphate having a Ca/P molar ratio of less than 1.67. Preferred poorly crystalline apatitic calcium phosphate compositions are described in, e.g., U.S. Pat. No. 6,027,742, U.S. Pat. No. 6,214,368, U.S. Pat. No. 6,287,341, U.S. Pat. No. 6,331,312, and U.S. Pat. No. 6,541,037, all of which are incorporated herein by reference.

A low temperature, high mechanical strength calcium phosphate composition can be used in combination with the DBM particles and, optionally, a cohesiveness agent, to prepare the implant material according to the invention. Such a low temperature high mechanical strength calcium phosphate composition is described in e.g., U.S. Pat. No. 5,783,217, which is incorporated herein by reference.

The amorphous calcium phosphate and the second calcium phosphate source can also be mixed to form a calcium phosphate powder using a high energy mixing process, for example high energy milling. Such high energy milling processes are referred to as "amorphization" processes because they decrease the crystallinity index of the calcium phosphate source particles. During amorphization, the calcium phosphate source particles experience multiple impacts with each other, and these impacts break down the particles into much smaller particles having high specific surface areas. The impacts and corresponding transfer of energy into the calcium phosphate source particles during amorphization may further cause changes in their structure and/or composition. The resulting calcium phosphate source particles are densely packed due to their small particle size, thereby improving the formability and cohesiveness of the bone implant materials of the invention. Further, the resulting calcium phosphate source particles react more efficiently to form hardened PCA calcium phosphate in vivo.

In high energy ball milling, the amorphous calcium phosphate and the second calcium phosphate source are placed in a container and ground by randomly moving balls agitated by rotating shafts or arms. Milling machines like those sold under the trademarks Attritor Model 01HD, Fritch Pulverisette 4, ASI Uni-Ball Mill II, and Zoz Simoloyer® may be used. The high energy milling breaks down the amorphous calcium phosphate and the second calcium phosphate source into nanostructural particles on the order of less than about 100 nanometers (nm) having a specific surface area between about 50 $m^2/g$ and about 150 $m^2/g$. The nanostructural particles are evenly mixed and form a high-density, homogeneous product powder, which lacks long-range crystalline order. High energy milling processes, including high energy ball milling, and their effects on calcium phosphate sources are further described in copending U.S. patent application Ser. No. 10/222,670, filed on Aug. 16, 2002, and entitled "Synthesis of Calcium Phosphates by Mechano-Chemical Process."

In at least some embodiments, the amorphous calcium phosphate and the second calcium phosphate source are milled for a time less than or equal to about 24 hours. In some embodiments, the amorphous calcium phosphate and the second calcium phosphate source are milled for about 15 hours. In other embodiments, the amorphous calcium phosphate and the second calcium phosphate source are milled for about 3 hours. As the high energy milling time increases, the amorphization of the amorphous calcium phosphate and the second calcium phosphate source increases and their X-ray diffraction pattern becomes broader and more diffuse (FIG. 1).

The DBM and the calcium phosphate powder are then combined. Any mixing method that achieves thorough and permanent blending of the DBM particles and the calcium phosphate powder may be employed. Such methods will be known to those of skill in the art. For example, the DBM particles and the calcium phosphate powder may be combined using a Turbula mixer.

The calcium phosphate powder will be present in varying amounts depending upon the intended use and desired characteristics of the implant material. In some embodiments, the calcium phosphate powder will be present in an amount between about 20 and about 90 weight percent of the powder component. In other embodiments, the calcium phosphate powder will be present in an amount between about 50 to about 99 weight percent of the powder component. In still other embodiments, the calcium phosphate powder will be present in an amount of about 30 weight percent of the powder component. In preferred embodiments, the calcium phosphate is present in an amount of about 85 weight percent and the DBM is present in an amount of about 15 weight percent.

According to some embodiments, the bone implant material additionally includes a biocompatible cohesiveness agent (e.g., a binder). In some instances, the DBM content of the bone implant material is so high that, notwithstanding the formability and cohesiveness provided by the high energy milled calcium phosphate powder, a cohesiveness agent may be desirable to further augment the mechanical strength of the bone implant material during implantation. Moreover, the inclusion of a cohesiveness agent permits the use of calcium phosphate powders other than those previously discussed without significantly diminishing the mechanical strength of the implant material. These alternative calcium phosphate powders need not be subjected to high energy milling processes. Thus, for example, in some embodiments, a calcium phosphate powder comprising an amorphous calcium phosphate and an acidic second calcium phosphate source that have not been high energy milled may be employed. Such materials are described, for example, in U.S. Pat. No. 6,214,368, the contents of which are incorporated herein by reference.

Non-limiting examples of suitable biocompatible cohesiveness agents include polymers selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof. In some embodiments, the biocompatible cohesiveness agent is water-soluble. A water-soluble cohesiveness agent dissolves from the implant material shortly after its implantation in vivo, thereby introducing macroporosity into the bone implant material. This macroporosity increases the osteoconductivity of the bone implant material by enhancing the access and, consequently, the remodeling activity of the osteoclasts and osteoblasts at the implant site.

The biocompatible cohesiveness agent may be added to the bone implant material in varying amounts and at a variety of stages during the production of the powder component. If included, the biocompatible cohesiveness agent is present in an amount less than or equal to 20 weight percent of the powder component (e.g., in an amount of less than about 1 wt %, 5 wt %, or 10 wt %, or in an amount in the range of about 1 to about 20 wt %). In particular embodiments, the biocompatible cohesiveness agent is present in an amount of about 10 weight percent of the powder component. In a preferred embodiment, the implant material includes DBM in an amount of about 50 weight percent, a calcium phosphate component in an amount of about 45 weight percent, and a cohesiveness agent in an amount of about 5 weight percent. The biocompatible cohesiveness agent may be added to the calcium phosphate sources before or after high energy milling. The biocompatible cohesiveness agent may be added to the DBM particles as a solution; for example, the cohesiveness agent can coat the DBM particles. The biocompatible cohesiveness agent may be added to the osteoinductive powder including the DBM particles and the calcium phosphate powder. Those of skill in the art will be able to determine the amount of cohesiveness agent and method of inclusion required for a given application.

The calcium phosphate compositions of the invention can also include biologically active agents. In general, the only requirement is that the substance remain active within the paste during fabrication or be capable of being subsequently activated or re-activated, or that the biologically active agent be added at the time of implantation of the self-hardening paste into a host or following hardening of the vehicle at 37 C in an aqueous environment.

Biologically active agents that can be incorporated into the compositions of the invention include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the compositions of the invention include, without limitation, anti-cancer agents, antibiotics, analgesics, anti-inflammatory agents, immunosuppressants, enzyme inhibitors, antihistamines, anti-convulsants, hormones, muscle relaxants, anti-spasmodics, ophthalmic agents, prostaglandins, anti-depressants, anti-psychotic substances, trophic factors, osteoinductive proteins, growth factors, and vaccines.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, TNF alpha agonists/antagonists, endothelin A receptor antagonists, retinoic acid receptor agonists, immuno-modulators, hormonal and antihormonal agents, photodynamic agents, and tyrosine kinase inhibitors.

Any of the biologically active agents listed in Table 1 can be used.

TABLE 1

| | | |
|---|---|---|
| Alkylating agents | cyclophosphamide | lomustine |
| | busulfan | procarbazine |
| | ifosfamide | altretamine |
| | melphalan | estramustine phosphate |
| | hexamethylmelamine | mechlorethamine |
| | thiotepa | streptozocin |
| | chlorambucil | temozolomide |
| | dacarbazine | semustine |
| | carmustine | |
| Platinum agents | cisplatin | carboplatinum |
| | oxaliplatin | ZD-0473 (AnorMED) |
| | spiroplatinum, | lobaplatin (Aeterna) |
| | carboxyphthalatoplatinum, | satraplatin (Johnson Matthey) |
| | tetraplatin | BBR-3464 (Hoffmann-La Roche) |
| | ormiplatin | SM-11355 (Sumitomo) |
| | iproplatin | AP-5280 (Access) |
| Antimetabolites | azacytidine | tomudex |
| | gemcitabine | trimetrexate |
| | capecitabine | deoxycoformycin |
| | 5-fluorouracil | fludarabine |
| | floxuridine | pentostatin |
| | 2-chlorodeoxyadenosine | raltitrexed |
| | 6-mercaptopurine | hydroxyurea |
| | 6-thioguanine | decitabine (SuperGen) |
| | cytarabin | clofarabine (Bioenvision) |
| | 2-fluorodeoxy cytidine | irofulven (MGI Pharma) |
| | methotrexate | DMDC (Hoffmann-La Roche) |
| | idatrexate | ethynylcytidine (Taiho) |
| Topoisomerase inhibitors | amsacrine | rubitecan (SuperGen) |
| | epirubicin | exatecan mesylate (Daiichi) |
| | etoposide | quinamed (ChemGenex) |
| | teniposide or mitoxantrone | gimatecan (Sigma-Tau) |
| | irinotecan (CPT-11) | diflomotecan (Beaufour-Ipsen) |
| | 7-ethyl-10-hydroxy-camptothecin | TAS-103 (Taiho) |
| | topotecan | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue (Exelixis) | CKD-602 (Chong Kun Dang) |
| | BBR-3576 (Novuspharma) | KW-2170 (Kyowa Hakko) |
| Antitumor antibiotics | dactinomycin (actinomycin D) | amonafide |
| | doxorubicin (adriamycin) | azonafide |
| | deoxyrubicin | anthrapyrazole |
| | valrubicin | oxantrazole |
| | daunorubicin (daunomycin) | losoxantrone |
| | epirubicin | bleomycin sulfate (blenoxane) |
| | therarubicin | bleomycinic acid |
| | idarubicin | bleomycin A |
| | rubidazone | bleomycin B |
| | plicamycinp | mitomycin C |
| | porfiromycin | MEN-10755 (Menarini) |
| | cyanomorpholinodoxorubicin | GPX-100 (Gem Pharmaceuticals) |
| | mitoxantrone (novantrone) | |

TABLE 1-continued

| | | |
|---|---|---|
| Antimitotic agents | paclitaxel | SB 408075 (GlaxoSmithKline) |
| | docetaxel | E7010 (Abbott) |
| | colchicine | PG-TXL (Cell Therapeutics) |
| | vinblastine | IDN 5109 (Bayer) |
| | vincristine | A 105972 (Abbott) |
| | vinorelbine | A 204197 (Abbott) |
| | vindesine | LU 223651 (BASF) |
| | dolastatin 10 (NCI) | D 24851 (ASTAMedica) |
| | rhizoxin (Fujisawa) | ER-86526 (Eisai) |
| | mivobulin (Warner-Lambert) | combretastatin A4 (BMS) |
| | cemadotin (BASF) | isohomohalichondrin-B (PharmaMar) |
| | RPR 109881A (Aventis) | ZD 6126 (AstraZeneca) |
| | TXD 258 (Aventis) | PEG-paclitaxel (Enzon) |
| | epothilone B (Novartis) | AZ10992 (Asahi) |
| | T 900607 (Tularik) | IDN-5109 (Indena) |
| | T 138067 (Tularik) | AVLB (Prescient NeuroPharma) |
| | cryptophycin 52 (Eli Lilly) | azaepothilone B (BMS) |
| | vinflunine (Fabre) | BNP-7787 (BioNumerik) |
| | auristatin PE (Teikoku Hormone) | CA-4 prodrug (OXiGENE) |
| | BMS 247550 (BMS) | dolastatin-10 (NIH) |
| | BMS 184476 (BMS) | CA-4 (OXiGENE) |
| | BMS 188797 (BMS) | |
| | taxoprexin (Protarga) | |
| Aromatase inhibitors | aminoglutethimide | exemestane |
| | letrozole | atamestane (BioMedicines) |
| | anastrazole | YM-511 (Yamanouchi) |
| | formestane | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | mafosfamide (Baxter International) |
| | glufosfamide (Baxter International) | apaziquone (Spectrum Pharmaceuticals) |
| | albumin + 32P (Isotope Solutions) | O6 benzyl guanine (Paligent) |
| | thymectacin (NewBiotics) | |
| | edotreotide (Novartis) | |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenics) | ISF-154 (Tragen) |
| | adenocarcinoma vaccine (Biomira) | cancer vaccine (Intercall) |
| | CTP-37 (AVI BioPharma) | norelin (Biostar) |
| | IRX-2 (Immuno-Rx) | BLP-25 (Biomira) |
| | PEP-005 (Peplin Biotech) | MGV (Progenics) |
| | synchrovax vaccines (CTL Immuno) | β-alethine (Dovetail) |
| | melanoma vaccine (CTL Immuno) | CLL therapy (Vasogen) |
| | p21 RAS vaccine (GemVax) | |
| Hormonal and antihormonal agents | estrogens | prednisone |
| | conjugated estrogens | methylprednisolone |
| | ethinyl estradiol | prednisolone |
| | chlortrianisen | aminoglutethimide |
| | idenestrol | leuprolide |
| | hydroxyprogesterone caproate | goserelin |
| | medroxyprogesterone | leuporelin |
| | testosterone | bicalutamide |
| | testosterone propionate; fluoxymesterone | flutamide |
| | methyltestosterone | octreotide |
| | diethystilbestrol | nilutamide |
| | megestrol | mitotane |
| | tamoxifen | P-04 (Novogen) |
| | toremofine | 2-methoxyestradiol (EntreMed) |
| | dexamethasone | arzoxifene (Eli Lilly) |

TABLE 1-continued

| | | |
|---|---|---|
| Photodynamic agents | talaporfin (Light Sciences)<br>Theralux (Theratechnologies)<br>motexafin gadolinium (Pharmacyclics) | Pd-bacteriopheophorbide (Yeda)<br>lutetium texaphyrin (Pharmacyclics)<br>hypericin |
| Tyrosine Kinase Inhibitors | imatinib (Novartis)<br>leflunomide (Sugen/Pharmacia)<br>ZD1839 (AstraZeneca)<br>erlotinib (Oncogene Science)<br>canertinib (Pfizer)<br>squalamine (Genaera)<br>SU5416 (Pharmacia)<br>SU6668 (Pharmacia)<br>ZD4190 (AstraZeneca)<br>ZD6474 (AstraZeneca)<br>vatalanib (Novartis)<br>PKI166 (Novartis)<br>GW2016 (GlaxoSmithKline)<br>EKB-509 (Wyeth)<br>EKB-569 (Wyeth) | kahalide F (PharmaMar)<br>CEP-701 (Cephalon)<br>CEP-751 (Cephalon)<br>MLN518 (Millenium)<br>PKC412 (Novartis)<br>phenoxodiol ( )<br>trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramisole, 10-(alpha-diethylaminopropionyl)-phenothiazine hydrochloride, calmidazolium chloride, hemicholinium-3, 3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, nonsteroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlornaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, transforming growth factors (beta), including beta-1, beta-2, beta-3, inhibin, and activin; and bone morphogenetic proteins such as OP-1, BMP-2 and BMP-7.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

Osteogenic Proteins

The biologically active agent is desirably selected from the family of proteins known as the transforming growth factors-beta (TGF-β) superfamily of proteins, which includes the activins, inhibins, and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins which may be useful as the active agent in the calcium phosphate compositions of the invention include Vgr-2, Jones et al., Mol. Endocrinol. 6:1961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention may be BIP, disclosed in WO94/01557; HP00269, disclosed in JP Publication number: 7-250688; and MP52, disclosed in PCT application WO93/16099. The disclosures of all of the above applications are incorporated herein by reference. A subset of BMPs which are presently preferred for use in the invention include BMP-2, BMP-4, BMP-5, BMP-6, BMP-7, BMP-10, BMP-12, BMP-13, BMP-14, and MP52. The active agent is most preferably BMP-2, the sequence of which is disclosed in U.S. Pat. No. 5,013,649, the disclosure of which is incorporated herein by reference. Other osteogenic agents known in the art can also be used, such as teriparatide (Forteo™), Chrysalin®, prostaglandin E2, or LIM protein, among others.

The biologically active agent may be recombinantly produced, or purified from a protein composition. The active agent, if a TGF-β, such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference.

The biologically active agent may further include additional agents such as the Hedgehog, Frazzled, Chordin, Noggin, Cerberus and Follistatin proteins. These families of proteins are generally described in Sasai et al., Cell 79:779-790 (1994) (Chordin); PCT Patent Publication WO94/05800 (Noggin); and Fukui et al., Devel. Biol. 159:131 (1993) (Follistatin). Hedgehog proteins are described in WO96/16668; WO96/17924; and WO95/18856. The Frazzled family of proteins is a recently discovered family of proteins with high homology to the extracellular binding domain of the receptor protein family known as Frizzled. The Frizzled family of genes and proteins is described in Wang et al., J. Biol. Chem. 271:4468-4476 (1996). The active agent may also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are hereby incorporated by reference herein. The amount of osteogenic protein effective to stimulate increased osteogenic activity of present or infiltrating progenitor or other cells will depend upon the size and nature of the defect being treated, as well as the carrier being employed. Generally, the amount of protein to be delivered is in a range of from about 0.1 to about 100 mg; preferably about 1 to about 100 mg; most preferably about 10 to about 80 mg.

Biologically active agents can be introduced into the calcium phosphate compositions of the invention during or after its formation. Agents may conveniently be mixed into the compositions prior to setting. Alternatively, the vehicle may be shaped and hardened and then exposed to the therapeutic agent in solution. This particular approach is particularly well suited for proteins, which are known to have an affinity for apatitic materials. A buffer solution containing the biologically active agent may be employed, instead of water, as the aqueous solution in which the self-hardening paste is, for example, irrigated prior to implantation. Buffers may be used in any pH range, but most often will be used in the range of 5.0 to 8.0 in preferred embodiments the pH will be compatible with prolonged stability and efficacy of the desired therapeutic agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for it's biocompatibility with the host tissues and its compatibility with the therapeutic agent. For most applications of nucleic acids, peptides or antibiotics a simple phosphate buffered saline will suffice.

Standard protocols and regimens for delivery of the above-listed agents are known in the art. Typically, these protocols are based on oral or intravenous delivery. Biologically active agents are introduced into the vehicle in amounts that allow delivery of an appropriate dosage of the agent to the implant site. In most cases, dosages are determined using guidelines known to practitioners and applicable to the particular agent in question. The exemplary amount of biologically active agent to be included in the paste of the invention or added to the hardened delivery vehicle is likely to depend on such variables as the type and extent of the condition, the overall health status of the particular patient, the formulation of the active agent, and the bioresorbability of the delivery vehicle used. Standard clinical trials may be used to optimize the dose and dosing frequency for any particular biologically active agent.

The invention also provides calcium phosphate compositions having a porous composition. Porosity of the calcium phosphate compositions is a desirable characteristic as it facilitates cell migration and infiltration into the calcium phosphate compositions so that the cells can secrete extracellular bone matrix. It also provide access for vascularization.

Porosity also provide high surface area for enhanced resorption and release of active substance, as well as increased cell-matrix interaction.

A highly porous implant can be achieved by addition of an effervescent agent to the calcium phosphate compositions. The effervescent agent may be a gas which is dissolved in the calcium phosphate composition prior to implantation. The gas may be dissolved in the calcium phosphate composition under pressure, i.e., by subjecting the composite material to a pressurized atmosphere of the gas, but which is inert to the cementing reaction. The gas is then liberated upon exposure to physiological temperatures (i.e., upon injection or implantation), due to the decrease in gas solubility with increased temperature. Under these circumstances, the gas dissolution and subsequent pore formation occurs only during hardening in vivo, and not prior to administration. This is especially attractive since pore formation is not desired to occur at room temperature in the syringe. Suitable gases include, without limitation, carbon dioxide, air, nitrogen, helium, oxygen, and argon. Alternatively, the effervescent agent is a solid material which liberates gas upon dissolution. For example, sodium bicarbonate evolves carbon dioxide gas as it converts to an unstable carbonic acid intermediate, which subsequently evolves carbon dioxide and water. Desirably, the sodium carbonate is present in the calcium phosphate compositions in an amount between 0.5 and 40% by weight. A more detailed description of the use of effervescent agents is found in U.S. Ser. No. 10/160,607, entitled "Calcuim phosphate delivery vehicles for osteoinductive proteins," filed May 31, 2002.

In at least some embodiments, a suitable amount of a physiologically-acceptable fluid is added to the powder component to produce a self-hardening paste or putty. Non-limiting examples of suitable physiologically-acceptable fluids include water, saline, and phosphate buffers. These paste compositions have improved flow characteristics compared to most previously-known bone implant materials, which are attributable to the inclusion of amorphous calcium phosphate and the nature of the calcium phosphate powder. Varying amounts of fluid may be added to the powder to produce a paste having the desired characteristics. For example, in at least some embodiments, 0.5-2.0 cc of fluid per gram of powder is used to prepare a paste that is formable, i.e., capable of being molded and retaining its shape. In at least some embodiments, the paste is injectable, i.e., capable of passing through a 16- to 18-gauge syringe.

Following the addition of the physiologically-acceptable fluid, the paste is delivered to the implant site. The paste may be injected into the implant site or formed into the desired shape and packed into the implant site. The paste may be formed into the desired shape and allowed to harden before being placed into the implant site. Pre-formed devices may be hand shaped, molded, or machined. Those of skill in the art will recognize implantation procedures appropriate for a given application.

The implant material demonstrates superior osteoinductivity in vivo as compared to isolated DBM alone. For example, upon implantation, a paste including (a) a powder component, including 60 weight percent DBM particles, 30 weight percent calcium phosphate powder, and 10 weight percent biocompatible cohesiveness agent selected from the group consisting of carboxymethylcellulose, polyvinylpyrrolidone, or mixtures thereof, and (b) 1 cc of a physiologically-acceptable fluid per gram powder component is more osteoinductive than DBM alone. Note that this superior osteoinductivity is observed despite the inclusion of the inorganic calcium phosphates, some of which have heretofore been known in the art to inhibit the osteoinductivity of DBM. Moreover, this paste retains its cohesiveness in vivo due to the high energy milled calcium phosphate powder and/or the inclusion of a biocompatible cohesiveness agent.

A paste of the bone implant material reacts ex vivo, i.e., pre-implantation, or in vivo, i.e., post-implantation, to form a poorly crystalline apatitic (PCA) calcium phosphate. The resultant PCA calcium phosphate possesses a nanometer-scale crystal structure that also approximates that of natural bone. For example, the crystals of the PCA calcium phosphate of the bone implant materials of the instant invention are about 26 nm in length and about 8 nm in width, while those of natural bone are between about 23 nm to about 32 nm in length and between about 6 nm and about 8 nm in width. The nanometer-scale crystal structure of the PCA calcium phosphate of the bone implant material provides a surface that is compatible with bone forming cells such as osteoclasts. Osteoclasts can attach and proliferate on the calcium phosphate substrate, which thereby serves as an osteoconductive material in vivo.

The PCA calcium phosphate product has a Ca/P molar ratio similar to that of naturally-occurring bone. The Ca/P molar ratio is between about 1.1 and about 1.9. In some embodiments, the Ca/P molar ratio is between 1.2 and 1.67. Preferably the Ca/P molar ratio is less than 1.67, and may be less than about 1.5. As previously discussed, the PCA calcium phosphate formation reaction proceeds substantially to completion; correspondingly, all or substantially all of the calcium and phosphate in the calcium phosphate sources of the osteoinductive powder become part of the PCA calcium phosphate product. Thus, the Ca/P molar ratio of the PCA calcium phosphate product may be controlled by the choice of calcium phosphate sources.

The conversion of the paste to PCA calcium phosphate occurs at ambient or body temperatures and is accompanied by hardening of the paste material. The hardening process is not adversely affected by the addition of DBM or the optional biocompatible cohesiveness agent. The "self-hardening" or "self-setting" reaction occurs slowly at ambient temperatures, i.e., between about 20° C. and 25° C., and is accelerated significantly at body temperatures, i.e., between about 32° C. and about 37° C. Thus, for example, the paste hardens at ambient temperatures after a time between about 20 minutes to about 60 minutes, while at body temperatures, the paste hardens after a time between about 3 minutes and about 15 minutes. The formation and characteristics of PCA calcium phosphates are further described in U.S. Pat. Nos. 6,214,368, 6,027,742, and 5,650,176, which are incorporated herein by reference.

The hardened PCA calcium phosphate implant materials display significant compressive strength, despite the inclusion of significant quantities of DBM (i.e., up to about 50 wt % of the powder component). Compressive strength is a particularly desirable attribute for certain types of bone implants, such as spinal implants. According to some embodiments, the PCA calcium phosphate bone implant materials have a compressive strength greater than about 1 MPa. In particular embodiments, the compressive strength is between 1 MPa and 20 MPa. In other particular embodiments, the compressive strength is between 2 MPa and 10 MPa.

Once the paste has converted to PCA calcium phosphate, the PCA calcium phosphate is remodeled into bone in vivo. As described above, the PCA calcium phosphate has a chemical composition and crystalline structure similar to that of natural bone and is resorbable in biological systems. Remodeling involves slow degradation of the PCA calcium phosphate and use by the body of the resulting calcium and phosphate materials to generate new bone. Remodeling of the bone implant materials prepared according to one or more embodiments of the invention is a long-term process, usually occurring on a time scale of months to years. Bone implant materials of higher densities require longer remodeling periods because the high density and low porosity of the implants slows penetration by cells and biological substances, causing remodeling to occur as a long-term inward diffusion process.

According to one or more embodiments, the present invention also provides a method of assaying the DBM content, by weight, in a given sample of a bone implant material. Given that the quantity of DBM affects the properties of the bone implant materials, a method that determines the quantity of DBM in a given material is desirable. The DBM content, by weight, in a given sample of a bone implant material may be measured in a DBM extraction assay. This assay utilizes hydrogen chloride (HCl) to digest the calcium phosphate sources in the bone implant material. Upon addition of HCl, the HCl-bone implant material mixture is agitated, centrifuged, and resuspended so as to form a pellet of extracted DBM, which may then be dried and weighed.

The invention is illustrated by the following examples, which are not intended to be limiting of the invention.

EXAMPLES

Example 1

Preparation of Demineralized Bone Matrix Fibers

This Example describes the preparation of DBM particles that are fibrous in nature.

Long bones were cleaned to remove all connective tissue. The end plates were removed to isolate the cortical bone component of the long bone, and the marrow was removed. The hollow long bones were washed in alcohol to further clean and remove fat. The bones were then turned on a lathe. Shavings were made by pressing a straight-edged silicon carbide cutting tool into the surface of the bone. The cutting tool advances along the length of the bone to provide a length of bone shaving. The rate of rotation of the bone in concert with the rate of motion of the cutting tool can be controlled by those familiar with the process so as to control the rate of material removal. Shavings of thickness varying between 50 µm and 250 µm, widths between 2 mm and 10 mm and random length were obtained by this process. These shaving were then washed in ether to remove the remaining fats. Demineralization was performed by stirring the shavings in 0.5 molar hydrochloric acid (HCl) for 1 hour. After demineralization, the fibers were rinsed in deionized water until the excess acid was removed. The fibers were then dried by rinsing in alcohol and ether and allowing the ether to evaporate. The average fiber length was distributed randomly between about 250 µm and 2 mm, and average fiber thickness was between about 50 µm and 250 µm.

Example 2

Preparation of Amorphous Calcium Phosphate

This Example describes the preparation of an amorphous calcium phosphate powder.

A solution of 1000 g of disodium hydrogen phosphate heptahydrate ($Na_2HPO_4 \cdot 7H_2O$) in 14.4 mL distilled water was prepared and stirred. To this solution, 555 g sodium hydroxide (NaOH), 333 g sodium bicarbonate ($NaHCO_3$), and 2.2 g sodium pyrophosphate decahydrate ($Na_4P_2O_7 \cdot 10H_2O$) were added sequentially to form solution 1.

A solution of 208 g of calcium nitrate tetrahydrate ($Ca(NO_3)_2 \cdot 4H_2O$) in 5.6 L of distilled water was prepared and stirred. 11 g of magnesium chloride hexahydrate ($MgCl_2 \cdot 6H_2O$) was added to this solution to form solution 2.

Solution 2 was quickly poured into solution 1 at room temperature and stirred for 1 minute. The amorphous calcium phosphate precipitated immediately and substantially completely. The pH of the suspension was 13±0.5, which was maintained to avoid conversion of the precipitate to an apatite or other more crystalline calcium phosphate.

The precipitate was then immediately separated from its mother solution using a basket centrifugal filtration process and washed using about 100 L of distilled water. Completion of the washing process was confirmed by the last wash ionic conductivity less than 300 µs. This process yields a gel cake of about 500 g of amorphous calcium phosphate.

The wet cake of amorphous calcium phosphate was immediately lyophilized so as to preserve the amorphous structure during drying. About 80% of the water was removed. About 100 g of the lyophilized powder was calcinated at 450° C. for 1 hour.

The amorphous calcium phosphate product had a Ca/P ratio of less than 1.5, and typically between 1.35 and 1.49.

Example 3

Preparation of Dicalcium Phosphate Dihydrate (DCPD)

This Example describes the preparation of dicalcium phosphate dihydrate powder.

20 g diammonium hydrogen phosphate ($(NH_4)_2HPO_4$) was dissolved in 1 L distilled water to prepare solution 3, having a concentration of 0.300 mol/L. It was verified that the pH of solution 3 was between 7.0 and 9.0.

35.5 g calcium nitrate tetrahydrate ($Ca(NO_3)_2 \cdot 4H_2O$) was dissolved in 0.5 L distilled water to prepare solution 4, having a concentration of 0.300 mol/L. It was verified that the pH of solution 4 was between 5.0 and 8.0.

Solution 4 was poured into solution 3, followed by stirring for about 2 minutes. It was verified that the pH of the resulting suspension was between 5.2 and 6.2. The suspension was filtered by vacuum filtration to form a uniform cake. The cake was washed three times with 750 mL distilled water (2.25 L total). When washing was complete, the cake was separated from the filter paper and dried in a laminar flow hood for 24 hours. The dried powder was milled through a 120 µm nominal pore size screen.

Example 4

Preparation of Calcium Phosphate Powder

This Example describes the preparation of a calcium phosphate powder comprising an amorphous calcium phosphate and a second calcium phosphate source.

Amorphous calcium phosphate, prepared as described in Example 2, and crystalline DCPD, prepared as described in Example 3, were combined in a 1:1 ratio by weight (e.g. 25 g each). The mixed powder was high energy milled in a Ball Mill at 100 RPM for about 3 hours. The average crystalline domain size of the resulting powder was less than about 100 nm.

Example 5

Preparation of DBM/Calcium Phosphate Powder

This Example describes the preparation of a powder comprising DBM particles and a calcium phosphate powder.

0.4 g fibrous DBM particles, prepared as described in Example 1, and 0.6 g calcium phosphate powder, prepared as described in Example 4, were combined using a Turbula mixer.

Example 6

Preparation DBM/Calcium Phosphate/Cohesiveness Agent Powder

This Example describes the preparation of a powder comprising DBM particles, a calcium phosphate powder, and a biocompatible cohesiveness agent.

0.5 g DBM particles, prepared as described in Example 1, 0.45 g calcium phosphate powder, prepared as described in Example 4, and 0.05 g Hercules 7 HFPH carboxymethylcellulose were combined in a silicone mixing bulb. The resulting powder contained about 50 wt % DBM particles, about 45 wt % calcium phosphate powder, and about 5 wt % carboxymethylcellulose.

Example 7

Preparation of Formable, Self-Hardening Paste

This Example describes the preparation of a formable, self-hardening paste from a DBM/calcium phosphate/cohesiveness agent powder.

1.0 g of the powder described in Example 6 was hydrated with 0.6 cc physiological saline per gram powder to form a paste. The resultant paste was formable, extrudable through a syringe, and hardened in less than 20 minutes at 37° C.

0.10 cc of the paste was extruded through a 1 cc Becton Dickinson slip tip syringe, having a cut-off tip, to form a 0.1 cc paste cylinder.

Example 8

Cohesiveness of Formable, Self-Hardening Paste

This Example describes the evaluation of the cohesiveness of a formable, self-hardening paste prepared according to the instant invention.

A 1.0 g sample of the paste prepared as described in Example 7 was formed into a ball about 1.0 cm in diameter, and the ball was dropped into a beaker of water. The ball retained its initial shape, without significant observable distortion, swelling, or mass loss, for at least 10 minutes. The sample was removed from the water, and the water was filtered to determine the extent of mass lost from the sample upon immersion. No measurable amount of mass loss was observed.

Example 9

Compressive Strength of CaP/DBM Composition

This Example describes the evaluation of the wet compressive strength of a formable, self-hardening paste prepared according to the instant invention.

Two grams of powder containing 0.3 g of DBM particles with a particle size ranging from 125 to 850 μm and 1.7 g calcium phosphate powder, prepared as described in Example 4, was hydrated with 0.5 cc physiological saline per gram powder to form a paste.

The paste was evenly loaded into 5 cylindrical stainless steel molds measuring 6 mm in diameter and 12 mm in height. The molds were then immersed into a 37° C. physiological saline bath for 2 hours.

The five hardened CaP/DBM samples were then removed from the molds and tested for compressive strength using a universal testing machine (Instron, Canton, Mass.) at a crosshead speed of 5 mm/minutes.

The average compressive strength was measured as 12±1 MPa.

Example 10

Hardening Times of Bone Implant Materials

Table 1 presents data regarding the hardening times of various bone implant materials prepared according to the instant invention.

TABLE 1

| % DBM in Ca/P Composition | Physiologically-Acceptable Fluid | Temperature | Setting Time (min.) | Hardening Time (min.) |
|---|---|---|---|---|
| HCS-24[1] 125-850 μm DBM (25%) | Saline | 37 | 7 | 9 |
| HCS-24 125-850 μm DBM (25%) | PBS 1:30[2] | 37 | 6 | 7 |
| HCS-24 125-850 μm DBM (25%) | Saline | 35 | 7 | 9 |
| HCS-24 125-850 μm DBM (25%) | PBS 1:30 | 35 | 6 | 7 |
| HCS-24 125-850 μm DBM (25%) | Saline | 33 | 8 | 10 |
| HCS-24 125-850 μm DBM (25%) | PBS 1:30 | 33 | 7 | 8 |
| HCS-24 50-250 μm DBM (25%) | Saline | 37 | 6 | 8 |
| HCS-24 50-250 μm DBM (25%) | PBS 1:30 | 37 | 5 | 6 |
| HCS-24 50-250 μm DBM (25%) | Saline | 35 | 6 | 8 |

TABLE 1-continued

| % DBM in Ca/P Composition | Physiologically-Acceptable Fluid | Temperature | Setting Time (min.) | Hardening Time (min.) |
|---|---|---|---|---|
| HCS-24 50-250 µm DBM (25%) | PBS 1:30 | 35 | 5 | 6 |
| HCS-24 50-250 µm DBM (25%) | Saline | 33 | 7 | 9 |
| HCS-24 50-250 µm DBM (25%) | PBS 1:30 | 33 | 6 | 9 |
| HCS-24 <125 µm DBM (25%) | Saline | 37 | 8 | 9 |
| HCS-24 <125 µm DBM (25%) | PBS 1:30 | 37 | 6 | 7 |
| HCS-24 <125 µm DBM (25%) | Saline | 35 | 10 | 15 |
| HCS-24 <125 µm DBM (25%) | PBS 1:30 | 35 | 7 | 10 |
| HCS-24 <125 µm DBM (25%) | Saline | 33 | 9 | 10 |
| HCS-24 <125 µm DBM (25%) | PBS 1:30 | 33 | 8 | 9 |

[1] "HCS-24" refers to high compressive strength, intimately mixed calcium phosphate sources that have been mixed for 24 hours.
[2] "PBS 1:30" refers to phosphate buffered solutions.

Example 11

Implantation of Bone Implant Materials

Assessment of ectopic bone formation after implantation in intramuscular or subcutaneous pockets within an athymic rat is the current standard for characterizing osteoinductive materials. This Example describes the use of the athymic rat model to assess bone implant materials prepared as described herein and to compare those compositions to other DBM formulations.

Six to seven week old male athymic rats (*Rattus norvegicus*, Crl:NIH-mu nudes, Charles River Laboratories) were housed and maintained in an isolator or microisolator equivalent under conditions recommended in the "Guide for the Care and Use of Laboratory Animals" (National Research Council, 1996). Rats were fed gamma-irradiated rodent chow and tap water ad libitum.

Various implant compositions as described herein were tested, as shown in Table 2. The inductivity of these implant compositions was compared to that of several implant materials known in the art: GRAFTON® DBM Putty (Osteotech, Inc.), GRAFTON® DBM Flex (Osteotech, Inc.), GRAFTON® DBM Matrix (Osteotech, Inc.), and Osteofil® (Regeneration Technologies, Inc.). All implants were implanted as a 0.1 cc cylinder having a 5 mm diameter.

Thirty-five (35) animals were randomly implanted with four different test articles, two in the thoracic musculature (pectoris major muscle) and two in the hind limbs (quadriceps). Each animal received an intraperitoneal (IP) injection of ketamine (100 mg/kg) and xylazine (10 mg/kg). Upon complete anesthetization, a small incision was made with a scalpel at the first implantation site, and the skin, subcutaneous tissue, and fascia were bisected with scissors. An intramuscular pouch was formed using pointed scissors to enter the desired muscle. The first cut was made in the same direction as the muscle fibers, and the scissors were spread to create a small pocket, which was held open while 0.1 ml of the test article was administered with forceps. Once the test article had solidified (at least 6 minutes), the muscle pocket was sutured closed. The surgery was then repeated at the remaining three implant sites. If necessary an additional half dose of ketamine/xylazine was administered to maintain anesthetization sufficient to complete the implantation procedure.

Daily clinical observations were performed on each animal for seven days post-implantation. Biweekly clinical observations were performed thereafter.

The test articles were retrieved six weeks following implantation. Animals were euthanized by $CO_2$ overdose immediately prior to retrieval. Tissue collections were limited to the implant material and approximately 0.5 cm margins of skeletal muscle and/or connective tissue. Tissue specimens were fixed in 10% neutral buffered formalin for a minimum of 12 hours and transferred in histological grade alcohol. Tissue specimens were bisected transversely at the implant midsection, routinely processed for paraffin embedding, cut onto glass slides, stained with hematoxylin and eosin, and cover-slipped. If necessary, tissue specimens were additionally decalcified prior to histologic analysis.

Randomized histological slides, each representing a different intramuscular implant section, were presented to a pathologist in a blind fashion with respect to the implant administered. The amount of bone formation was scored using a 0-4 scale, with 0 indicating no evidence of bone formation, and 1, 2, 3, and 4 indicating <25%, 26-50%, 51-75%, and >75% of implant surface involved in new bone formation, respectively. New bone lined with osteoblasts and/or containing osteocytes within lacunae and cartilaginous cells with their matrix and bone marrow surrounded with trabeculae of new bone were all regarded as part of the bone neoformation process. The shape and size of the implant (relative to the original 5 mm cylinder), the distribution of new bone in the implant, and the nature of the implant matrix were also noted. Once the evaluation of the slides was completed, the key to group assignment was provided to the evaluator to summarize the results, which are provided below.

TABLE 2

Bone Induction Scores for Selected DBM - Calcium Phosphate Formulations

| Amount DBM[3] | DBM Type, Size (μm) | Amount Cohesiveness Agent | Cohesiveness Agent Type | Amount Calcium Phosphate Powder | Bone Inductivity Score (0-4) |
|---|---|---|---|---|---|
| 30 | Particles, 125-850 | 15 | CMC[4] Powder | 55 | 0.6 |
| 50 | Particles, 125-850 | 15 | CMC Powder | 35 | 0.8 |
| 40 | Fibers, 250-2 mm | 0 | — | 60 | 0.8 |
| 50 | Particles, 53-125 | 5 | CMC Powder | 45 | 1.0 |
| 50 | Particles, 125-850 | 5 | CMC Powder | 45 | 1.6 |
| 50 | Particles, 500-850 | 5 | CMC Powder | 45 | 1.8 |
| 50 | Particles, 125-850 | 0 | — | 50 | 1.0 |
| 50 | Particles, 125-850 | 5 | CMC Powder | 45 | 1.0 |
| 60 | CMC Coated Particles, 125-850 | 0 | — | 40 | 1.0 |
| 60 | CMC Coated Particles, 125-850 | 10 | CMC Powder | 30 | 1.0 |
| 40 | Fibers, 250-2 mm | 5 | CMC Powder | 55 | 1.3 |
| 70 | Particles, 125-850 | 5 | CMC Powder | 25 | 2.0 |
| 60 | Particles, 125-850 | 10 | PVP[5] | 30 | 2.0 |
| 60 | Particles, 53-125 | 10 | CMC Powder | 30 | 3.0 |
| 60 | Particles, 125-850 | 10 | CMC Powder | 30 | 2.0 |
| | GRAFTON ® DBM Putty | | | | 2.7 |
| | GRAFTON ® DBM Flex | | | | 0.8 |
| | GRAFTON ® DBM Matrix | | | | 0.5 |
| | Osteofil ® | | | | 0.8 |

[3]Amounts of DBM, Binder, and Calcium Phosphate Powder are provided as weight percentages of the powder component of the implant material.
[4]CMC denotes carboxymethylcellulose.
[5]PVP denotes polyvinylpyrrolidone.

Example 12

DBM Extraction Assay

A 1.00 g sample of a DBM/calcium phosphate powder, prepared as described in Example 5, was placed into a 50 cc centrifuge tube. Twenty milliliters of 5N HCl was added to the sample. The sample was gently agitated for 20 minutes to digest the calcium phosphate material. The sample was then centrifuged for 5 minutes to form a DBM pellet, and the supernatant carefully poured off. The DBM pellet was resuspended twice in 15 mL DI-$H_2O$ and then once in 15 mL ethanol, centrifuging 10 minutes each time to separate the DBM. The excess ethanol was evaporated overnight, and the sample was dried for 24 hours in a vacuum drier. The extracted DBM was then weighed, resulting in 0.39 g of DBM.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. An osteoinductive powder comprising:
   (a) demineralized bone matrix (DBM) in an amount in the range of 40 to 70 wt %, wherein said DBM comprises particles having a particle size in the range of about 53 μm to about 850 μm, and
   (b) a calcium phosphate powder in an amount in the range of about 25 to about 60 wt %,
   wherein said osteoinductive powder forms a formable, self-hardening, poorly crystalline apatitic (PCA) calcium phosphate paste when admixed with a physiologically acceptable liquid, and wherein said paste is capable of hardening to form a PCA calcium phosphate having a compressive strength of greater than at least about 1 MPa.

2. The osteoinductive powder of claim 1, wherein said DBM comprises about 60 wt % of said osteoinductive powder.

3. The osteoinductive powder of claim 2, wherein said DBM comprises about 50 wt % of said osteoinductive powder.

4. The osteoinductive powder of claim 1, wherein said DBM comprises particles having a particle size in the range of about 125 to about 850 μm.

5. The osteoinductive powder of claim 1, wherein said DBM comprises particles having a particle size in the range of about 53 to about 125 μm.

6. The osteoinductive powder of claim 1, wherein said calcium phosphate powder comprises amorphous calcium phosphate and a second calcium phosphate.

7. The osteoinductive powder of claim 6, wherein said second calcium phosphate is an acidic or a neutral calcium phosphate.

8. The osteoinductive powder of claim 7, wherein said acidic calcium phosphate is calcium metaphosphate, dicalcium phosphate dihydrate, heptacalcium phosphate, tricalcium phosphate, calcium pyrophosphate dihydrate, poorly crystalline hydroxyapatite, calcium pyrophosphate, or octacalcium phosphate.

9. The osteoinductive powder of claim 8, wherein said acidic calcium phosphate is dicalcium phosphate dihydrate (DCPD).

10. The osteoinductive powder of claim 6, wherein said amorphous calcium phosphate and said second calcium phosphate have an average crystalline domain size of less than about 100 nm.

11. The osteoinductive powder of claim 1, wherein said calcium phosphate powder is subjected to a high energy milling process prior to admixing with said DBM particles.

12. The osteoinductive powder of claim 1 further comprising at least one supplemental material selected from a cohesiveness agent, a biologically active agent, and an effervescent agent.

13. The osteoinductive powder of claim 12, wherein said cohesiveness agent comprises about 0.5 to about 20 wt % of said osteoinductive powder.

14. The osteoinductive powder of claim 12, wherein said cohesiveness agent comprises less than about 20 wt % of said osteoinductive powder.

15. The osteoinductive powder of claim 14, wherein said cohesiveness agent comprises less than about 10 wt % of said osteoinductive powder.

16. The osteoinductive powder of claim 15, wherein said cohesiveness agent comprises less than about 5 wt % of said osteoinductive powder.

17. The osteoinductive powder of claim 16, wherein said cohesiveness agent comprises less than about 1 wt % of said osteoinductive powder.

18. The osteoinductive powder of claim 12, wherein said cohesiveness agent is a polymer selected from polysaccharides, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, and copolymers thereof.

19. The osteoinductive powder of claim 12, wherein said cohesiveness agent is selected from alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, and mixtures thereof.

20. The osteoinductive powder of claim 19, wherein said cellulose is methylcellulose, carboxy methylcellulose, hydroxypropyl methylcellulose, or hydroxyethyl cellulose.

21. The osteoinductive powder of claim 19, wherein said dextran is $\alpha$-cyclodextrin, $\beta$-cyclodextrin, $\gamma$-cyclodextrin, or sodium dextran sulfate.

22. The osteoinductive powder of claim 19, wherein said starch is hydroxyethyl starch or starch soluble.

23. The osteoinductive powder of claim 12, wherein said biologically active agent is selected from an antibody, an antibiotic, a polynucleotide, a polypeptide, a protein, an anti-cancer agent, a growth factor, and a vaccine.

24. The osteoinductive powder of claim 23, wherein said protein is an osteogenic protein.

25. The osteoinductive powder of claim 24, wherein said osteogenic protein is selected from BMP-2, BMP-4, BMP-5, BMP-6, BMP-7, BMP-10, BMP-12, BMP-13, and BMP-14.

26. The osteoinductive powder of claim 23, wherein said anti-cancer agent is selected from alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, tumor necrosis factor (TNF) alpha agonists, tumor necrosis factor (TNF) alpha antagonists, endothelin A receptor antagonists, retinoic acid receptor agonists, immuno-modulators, hormonal agents, antihormonal agents, photodynamic agents, and tyrosine kinase inhibitors.

27. The osteoinductive powder of claim 12, wherein said effervescent agent is sodium bicarbonate, carbon dioxide, air, nitrogen, helium, oxygen, or argon.

28. The osteoinductive powder of claim 27, wherein said effervescent agent comprises about 1 to about 40 wt % of said osteoinductive powder.

29. The osteoinductive powder of claim 1, wherein said paste hardens to form a PCA calcium phosphate having an overall Ca/P ratio of less than about 1.67.

30. The osteoinductive powder of claim 29, wherein said paste hardens to form a PCA calcium phosphate having an overall Ca/P ratio of less than about 1.5 when admixed with said physiologically acceptable liquid.

31. The osteoinductive powder of claim 1, wherein said paste hardens to form a PCA calcium phosphate having an overall Ca/P ratio in the range of about 1.0 to about 1.67 when admixed with said physiologically acceptable liquid.

32. An osteoinductive powder comprising:
(a) demineralized bone matrix (DBM) in an amount in the range of 40 to 70 wt %, wherein said DBM comprises particles having a particle size in the range of about 53 μm to about 850 μm;
(b) a calcium phosphate powder in an amount in the range of about 25 to about 60 wt %; and
(c) a biocompatible cohesiveness agent in an amount in the range of about 0.5 to 20 wt %;
wherein said osteoinductive powder forms a formable, self-hardening, poorly crystalline apatitic (PCA) calcium phosphate paste when admixed with a physiologically acceptable liquid, and wherein said paste is capable of hardening to form a PCA calcium phosphate having a compressive strength of greater than at least about 1 MPa.

33. A formable, self-hardening, poorly crystalline apatitic (PCA) calcium phosphate paste suitable for use as a bone implant material comprising:
(a) a powder component comprising:
(i) demineralized bone matrix (DBM) in an amount in the range of 40 to 70 wt %, wherein said DBM comprises particles having a particle size in the range of about 53 μm to about 850 μm, and (ii) a calcium phosphate powder in an amount in the range of about 25 to about 60 wt %; and (b) a physiologically-acceptable fluid in an amount to produce a cohesive, formable paste, wherein said paste retains its cohesiveness when introduced at an implant site in vivo and hardens to form a PCA calcium phosphate having a compressive strength of greater than at least about 1 MPa.

34. The paste of claim 33, wherein said DBM comprises about 60 wt % of said powder component.

35. The paste of claim 34, wherein said DBM comprises about 50 wt % of said powder component.

36. The paste of claim 33, wherein said DBM comprises particles having a particle size in the range of about 125 to about 850 µm.

37. The paste of claim 33, wherein said DBM comprises particles having a particle size in the range of about 53 to about 125 µm.

38. The paste of claim 33, wherein said calcium phosphate powder comprises amorphous calcium phosphate and a second calcium phosphate.

39. The paste of claim 38, wherein said second calcium phosphate is an acidic or a neutral calcium phosphate.

40. The paste of claim 39, wherein said acidic calcium phosphate is calcium metaphosphate, dicalcium phosphate dihydrate, heptacalcium phosphate, tricalcium phosphate, calcium pyrophosphate dihydrate, poorly crystalline hydroxyapatite, calcium pyrophosphate, or octacalcium phosphate.

41. The paste of claim 40, wherein said acidic calcium phosphate is dicalcium phosphate dihydrate (DCPD).

42. The paste of claim 38, wherein said amorphous calcium phosphate and said second calcium phosphate have an average crystalline domain size of less than about 100 nm.

43. The paste of claim 33, wherein said calcium phosphate powder is subjected to a high energy milling process prior to admixing with said DBM particles.

44. The paste of claim 33 further comprising at least one supplemental material selected from a cohesiveness agent, a biologically active agent, and an effervescent agent.

45. The paste of claim 44, wherein said cohesiveness agent comprises about 0.5 to about 20 wt % of said powder component.

46. The paste of claim 44, wherein said cohesiveness agent comprises less than about 20 wt % of said powder component.

47. The paste of claim 46, wherein said cohesiveness agent comprises less than about 10 wt % of said powder component.

48. The paste of claim 47, wherein said cohesiveness agent comprises less than about 5 wt % of said powder component.

49. The paste of claim 48, wherein said cohesiveness agent comprises less than about 1 wt % of said powder component.

50. The paste of claim 44, wherein said cohesiveness agent is a polymer selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly(ϵ-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers thereof.

51. The paste of claim 44, wherein said cohesiveness agent is selected from alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, and mixtures thereof.

52. The paste of claim 51, wherein said cellulose is methylcellulose, carboxy methylcellulose, hydroxypropyl methylcellulose, or hydroxyethyl cellulose.

53. The paste of claim 51, wherein said dextran is α-cyclodextrin, β-cyclodextrin, γ-cyclodextrin, or sodium dextran sulfate.

54. The paste of claim 51, wherein said starch is hydroxyethyl starch or starch soluble.

55. The paste of claim 46, wherein said biologically active agent is selected from an antibody, an antibiotic, a polynucleotide, a polypeptide, a protein, an anti-cancer agent, a growth factor, and a vaccine.

56. The paste of claim 55 wherein said protein is an osteogenic protein.

57. The paste of claim 56, wherein said osteogenic protein is selected from BMP-2, BMP-4, BMP-5, BMP-6, BMP-7, BMP-10, BMP-12, BMP-13, and BMP-14.

58. The paste of claim 55, wherein said anti-cancer agent is selected from alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, tumor necrosis factor (TNF) alpha agonists, tumor necrosis factor (TNF) alpha antagonists, endothelin A receptor antagonists, retinoic acid receptor agonists, immuno-modulators, hormonal agents, antihormonal agents, photodynamic agents, and tyrosine kinase inhibitors.

59. The paste of claim 44, wherein said effervescent agent is sodium bicarbonate, carbon dioxide, air, nitrogen, helium, oxygen, or argon.

60. The paste of claim 59, wherein said effervescent agent comprises about 1 to about 40 wt % of said powder component.

61. The paste of claim 33, wherein said paste self-hardens to a PCA calcium phosphate having an overall Ca/P ratio of less than about 1.67.

62. The paste of claim 61, wherein said paste self-hardens to a PCA calcium phosphate having an overall Ca/P ratio of less than about 1.5.

63. The paste of claim 33, wherein said paste self-hardens to a PCA calcium phosphate having an overall Ca/P ratio in the range of about 1.0 to about 1.67.

64. The paste of claim 33, wherein said paste hardens to form a PCA calcium phosphate having a compressive strength in the range of about 1 MPa to about 20 MPa.

65. The paste of claim 64, wherein said paste hardens to form a PCA calcium phosphate having a compressive strength in the range of about 2 MPa to about 10 MPa.

66. The paste of claim 33, wherein said paste hardens to form a PCA calcium phosphate having a compressive strength of about 2 MPa.

67. A formable, self-hardening, poorly crystalline apatitic (PCA) calcium phosphate paste suitable for use as a bone implant material comprising:
- (a) a powder component, including:
  - (i) demineralized bone matrix (DBM) in an amount in the range of 40 to 70 wt %, wherein said DBM comprises particles having a particle size in the range of about 53 µm to about 850 µm,
  - (ii) a calcium phosphate powder in an amount in the range of about 25 to about 60 wt %, and
  - (iii) a biocompatible cohesiveness agent in an amount in the range of about 0.5 to 20 wt %; and
- (b) a physiologically acceptable fluid in an amount to produce a cohesive, formable paste, wherein said paste retains its cohesiveness when introduced at an implant site in vivo and hardens to form a PCA calcium phosphate having a compressive strength of greater than at least about 1 MPa.

68. A formable, self-hardening, poorly crystalline apatitic (PCA) calcium phosphate paste suitable for use as a bone implant material comprising:
- (a) a powder component, comprising:
  - (i) demineralized bone matrix (DBM) in an amount in the range of 40 wt % to 70 wt % of said powder component, wherein said DBM comprises particles having a particle size in the range of about 53 µm to about 850 µm, and
  - (ii) a calcium phosphate powder in an amount in the range of about 25 wt % to about 60 wt % of said powder component, wherein said calcium phosphate powder comprises an amorphous calcium phosphate and a second calcium phosphate having an average crystalline domain size of less than about 100 nm, and
- (b) a physiologically acceptable fluid in an amount to produce a coherent, formable paste, wherein said paste retains its cohesiveness when introduced at an implant site in vivo and hardens to form a poorly crystalline apatitic (PCA) calcium phosphate having a compressive strength between about 1 MPa and about 20 MPa.

69. The paste of claim 68 further comprising a biocompatible cohesiveness agent in an amount in the range of about 0.5 wt % to about 20 wt % of said powder component.

70. A bone implant material comprising a poorly crystalline apatitic (PCA) calcium phosphate, wherein said PCA calcium phosphate is formed by combining:
- (a) a powder component comprising:
  - (i) demineralized bone matrix (DBM) in an amount in the range of 40 wt % to 70 wt % of said powder component, wherein said DBM comprises particles having a particle size in the range of about 53 µm to about 850 µm,
  - (ii) a calcium phosphate powder comprising an amorphous calcium phosphate and a second calcium phosphate source, wherein said second calcium phosphate source is an acidic calcium phosphate, and
  - (iii) a biocompatible cohesiveness agent; and
- (b) a physiologically-acceptable fluid,
wherein said powder component and said liquid combine to produce a paste that hardens to form a PCA calcium phosphate having a compressive strength between about 1 MPa and about 20 MPa.

71. A method of bone repair comprising introducing the bone implant material of claim 33 into a patient in need thereof at a site requiring bone repair, wherein, upon hardening, said bone implant material has a compressive strength between about 1 MPa and about 20 MPa.

72. The osteoinductive powder of claim 1, wherein said paste is capable of hardening to form a PCA calcium phosphate having a compressive strength of between about 1 MPa and 20 MPa.

73. The osteoinductive powder of claim 1, wherein said paste is capable of hardening to form a PCA calcium phosphate having a compressive strength of between about 2 MPa and 10 MPa.

74. The osteoinductive powder of claim 32, wherein said paste is capable of hardening to form a PCA calcium phosphate having a compressive strength of between about 1 MPa and 20 MPa.

75. The osteoinductive powder of claim 32, wherein said paste is capable of hardening to form a PCA calcium phosphate having a compressive strength of between about 2 MPa and 10 MPa.

76. The paste of claim 33, wherein said paste hardens to form a PCA calcium phosphate having a compressive strength of between about 1 MPa and 20 MPa.

77. The paste of claim 33, wherein said paste hardens to form a PCA calcium phosphate having a compressive strength of between about 2 MPa and 10 MPa.

78. The paste of claim 67, wherein said paste hardens to form a PCA calcium phosphate having a compressive strength of between about 1 MPa and 20 MPa.

79. The paste of claim 67, wherein said paste hardens to form a PCA calcium phosphate having a compressive strength of between about 2 MPa and 10 MPa.

80. The paste of claim 68, wherein said paste hardens to form a PCA calcium phosphate having a compressive strength of between about 2 MPa and 10 MPa.

81. The bone implant material of claim 70, wherein said paste hardens to form a PCA calcium phosphate having a compressive strength of between about 2 MPa and 10 MPa.

82. The method of claim 71, wherein, upon hardening, said bone implant material has a compressive strength of between about 2 MPa and 10 MPa.

83. The osteoinductive powder of claim 1, wherein said DBM comprises fibers.

84. The osteoinductive powder of claim 83, wherein said DBM fibers have a length between about 50 µm and 3 mm and an aspect ratio of greater than 4.

85. The osteoinductive powder of claim 32, wherein said DBM comprises fibers.

86. The osteoinductive powder of claim 85, wherein said DBM fibers have a length between about 50 µm and 3 mm and an aspect ratio of greater than 4.

87. The paste of claim 33, wherein said DBM comprises fibers.

88. The paste of claim 87, wherein said DBM fibers have a length between about 50 µm and 3 mm and an aspect ratio of greater than 4.

89. The paste of claim 67, wherein said DBM comprises fibers.

90. The paste of claim 89, wherein said DBM fibers have a length between about 50 µm and 3 mm and an aspect ratio of greater than 4.

91. The paste of claim 68, wherein said DBM comprises fibers.

92. The paste of claim 91, wherein said DBM fibers have a length between about 50 µm and 3 mm and an aspect ratio of greater than 4.

93. The bone implant material of claim 70, wherein said DBM comprises fibers.

94. The bone implant material of claim 93, wherein said DBM fibers have a length between about 50 µm and 3 mm and an aspect ratio of greater than 4.

* * * * *